United States Patent [19]
Marangos et al.

[11] Patent Number: 6,011,017
[45] Date of Patent: Jan. 4, 2000

[54] METHOD OF REDUCING PULMONARY HYPERTENSION AND ATRIAL FIBRILLATION AFTER SURGERY USING CARDIOPULMONARY BYPASS

[75] Inventors: Paul J. Marangos, La Costa; Anthony W. Fox, Rancho LaCosta, both of Calif.; Bernhard Riedel; David Royston, both of Harefield, United Kingdom

[73] Assignee: Cypros Pharmaceutical Corp., Carlsbad, Calif.

[21] Appl. No.: 09/060,773

[22] Filed: Apr. 15, 1998

[51] Int. Cl.$^7$ ............................ A61K 31/70; C07H 11/04
[52] U.S. Cl. .............................................. 514/23; 536/117
[58] Field of Search ............................... 514/23; 536/117

[56] References Cited

U.S. PATENT DOCUMENTS

| | | |
|---|---|---|
| 4,546,095 | 10/1985 | Markov . |
| 4,703,040 | 10/1987 | Markov ..................................... 514/23 |
| 5,039,665 | 8/1991 | Markov . |
| 5,506,210 | 4/1996 | Parish et al. . |
| 5,731,291 | 3/1998 | Sullivan et al. . |

FOREIGN PATENT DOCUMENTS 3323850   1/1985   Germany .

OTHER PUBLICATIONS

Angelos, M.G., et al, "Fructose–1, 6–diphosphate fails to limit early myocardial infarction size in a canine model," *Ann. Emerg. Med.* 22: 171–177 (1993).

Brunswick, R., et al, "Preservation of myocardium by infusion of fructose diphosphate following coronary occlusion," abstract, *Am J Cardiol 49*: 1008 (1982).

Cargnoni, A., et al, "Role of timing of administration in the cardioprotective effect of fructose–1,6–bisphosphate," *Cardiovasc Drugs Ther 6*: 209–17 (1992).

Conti, V.R., et al, "Metabolic and functional effects of carbohydrate substrate with single–dose and multiple–dose potassium cardioplegia," *Ann. Thoracic Surg. 36*: 320–327 (1983).

Eddy, L.J., et al, "Lack of a direct metabolic effect of fructose, 1,6–diphosphate in ischemic myocardium," *Am J Physiol 241*: H576–83 (1995).

Farias, L.A., et al, "Effects of fructose–1,6–diphosphate, glucose and saline on cardiac resuscitation," *Anesthesiology 65*: 595–601 (1986).

(List continued on next page.)

*Primary Examiner*—Gary L. Kunz
*Assistant Examiner*—Everett White
*Attorney, Agent, or Firm*—Patrick D. Kelly

[57] ABSTRACT

A method is disclosed for using fructose-1,6-diphosphate (FDP) to reduce and prevent two very serious problems caused by surgery that requires cardiopulmonary bypass. Before bypass begins, a liquid that contains FDP is intravenously injected into the patient, preferably over a period such as about 10 to 30 minutes, to allow the FDP to permeate in significant quantity into the heart and lungs while the heart is still beating. FDP can be added to the cardioplegia solution that is pumped through the heart to stop the heartbeat, and/or during bypass. This treatment was found to reduce two very important and serious problems that have unavoidably plagued CPB surgery in the past, which are: (1) elevated levels of pulmonary vascular resistance (PVR), which includes pulmonary hypertension; and (2) high occurrence rates for atrial fibrillation. Prior to this discovery, there has never been any satisfactory treatment which could reduce the severity and occurrence rates for these two major problems. FDP also can be co-administered in this manner, along with (1) a buffering or alkalizing agent that counteracts acidosis, such as sodium bicarbonate or THAM, and/or (2) a drug that reduces the formation of lactic acid, such as dichloroacetate.

12 Claims, 8 Drawing Sheets

% PATIENTS WITH ATRIAL FIBRILLATION
IN PHASE 2 CLINICAL TRIALS OF FDP

OTHER PUBLICATIONS

Granot, H., et al, "Successful treatment of irreversible hemorrhagic shock in dogs with fructose–1,6 diphosphate and dichloroacetate," *Circ Shock* 163–73 (1985).

Haasinen, I.E., et al, "Mechanism of the effect of exogenous FDP on myocardial energy metabolism," *Circulation 83*: 584–593 (1991).

Lazzarino G., et al, "Protective effects of exogenously administered fructose–1,6–diphosphate from ischemia reperfusion damage induced on isolated rat heart," *Ital J Biochem 38*: 251A–253A (1989).

Lazzarino, G., et al, "Ischemia and reperfusion: effect of fructose–1,6–bisphosphate," *Free Radic Res Commun 16*: 325–39 (1992).

Marchionni, N., et al, "Hemodynamic and electrocardio-–graphic effects of fructose–1,6–diphosphate in acute myocardial infarction," *Am J Cardiol 56*: 266–269 (1985).

Markov, A.K., et al, "Prevention of arrhythmias with fructose diphosphate in acute myocardial ischemia," abstract, *Circulation 62*: III–143 (1980).

Markov, A.K., et al, "Hemodynamic, electrocardiographic, and metabolic effects of fructose diphosphate on acute myocardial ischemia," *Am Heart J 100*: 639–46 (1980).

Markov, A.K., "Hemodynamics and metabolic effects of fructose 1–6 diphosphate in ischemia and shock—experimental and clinical observations," *Ann Emerg Med 15*: 1470–7 (1986).

Markov, A.K., et al, "Increasing survival of dogs subjected to hemorrhagic shock by administration of fructose 1–6 diphosphate," *Surgery 102*: 515–27 (1987).

Markov, A.K., et al, "Improvement of hemodynamics and pulmonary function following fructose 1–6 diphosphate adminisration in ARDS patients," *Microcirculation 1*: 173–178 (1987).

Pasque, M.K., et a, "Metabolic intervention to affect myocardial recovery following ischemia," *Annals of Surgery 200*: 1–12 (1984).

Sernov, L.N., et al, "The characteristics of the cardioprotective action of fructose–1,6–diphosphate," *Biull Eksp Biol Med 111*:172–3 (1991) (abstract).

Sernov, L.N., et al, "The antiacidotic and cardio–protective effects of fructose–1,6–diphosphate and dehydroascorbic acid," *Farmakol Toksikol 54*:24–26 (1991) (abstract).

Sernov, L.N., et al, "A comparative evaluation of the cardioprotective and antianginal actions of energy–providing agents," *Eksp Klin Farmakol 55*:13–15 (1992) (abstract).

Stryer, L., *Biochemistry*, 2nd ed., pp. 266–267 (Freeman & Co., San Francisco, 1981).

Zhang, J.N., et al, "Protective effect of exogenous fructose–1,6–diphosphate in cardiogenic shock," *Cardiovasc Res 22*: 927–32 (1988).

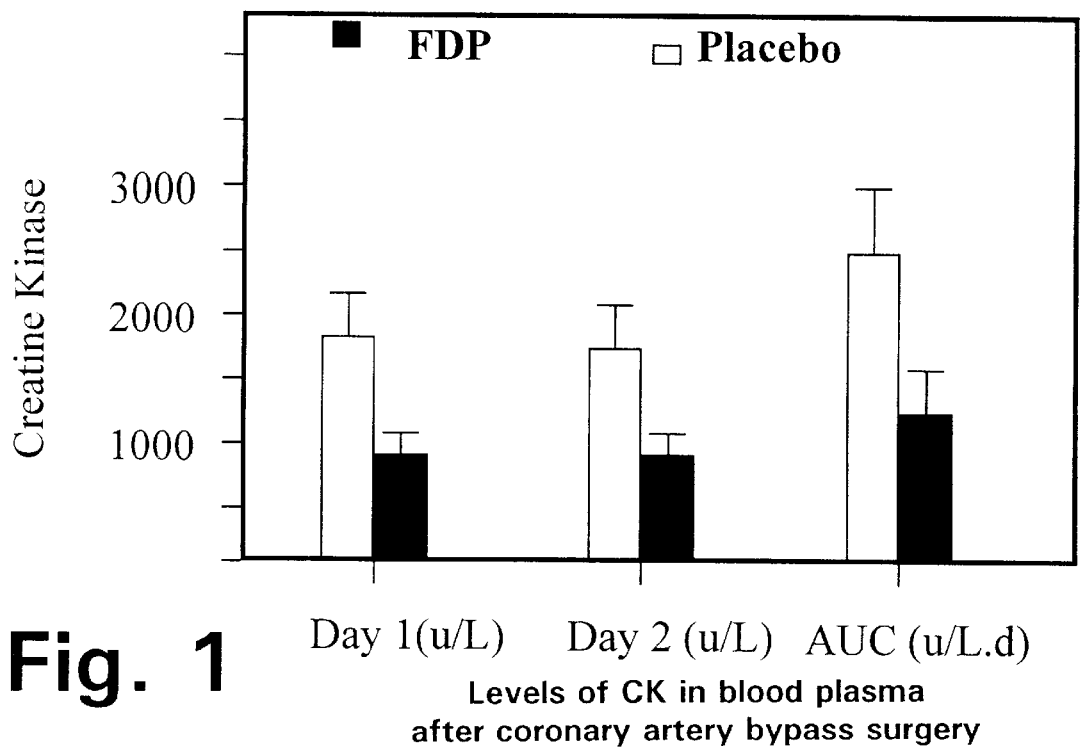
Fig. 1 Levels of CK in blood plasma after coronary artery bypass surgery
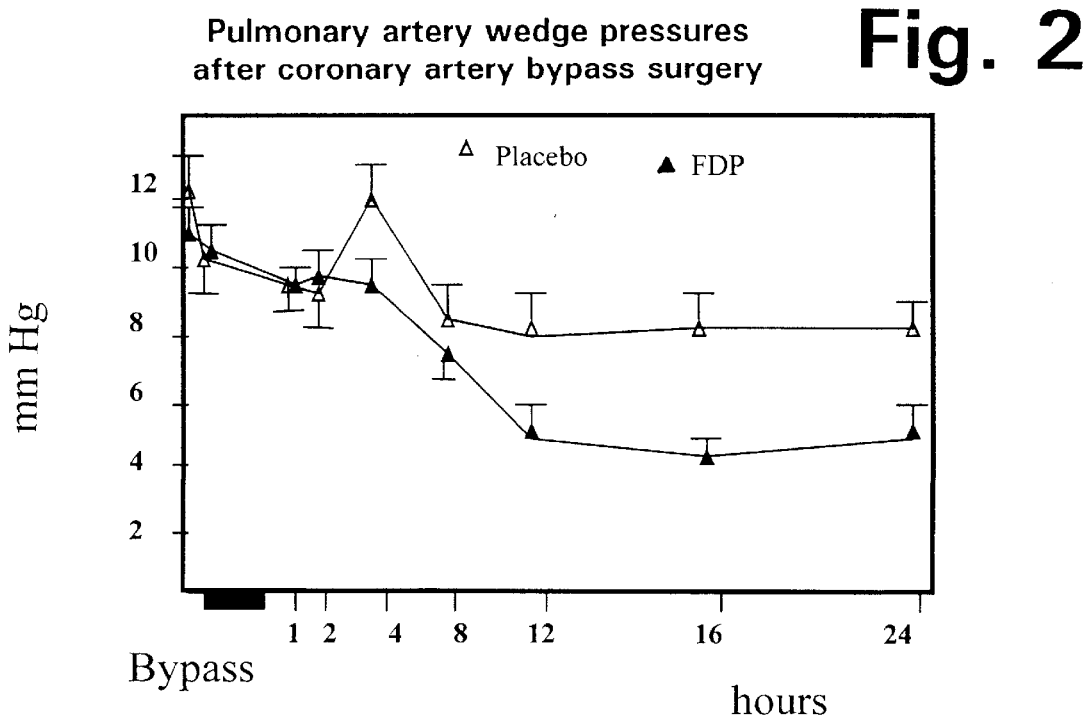
Fig. 2 Pulmonary artery wedge pressures after coronary artery bypass surgery

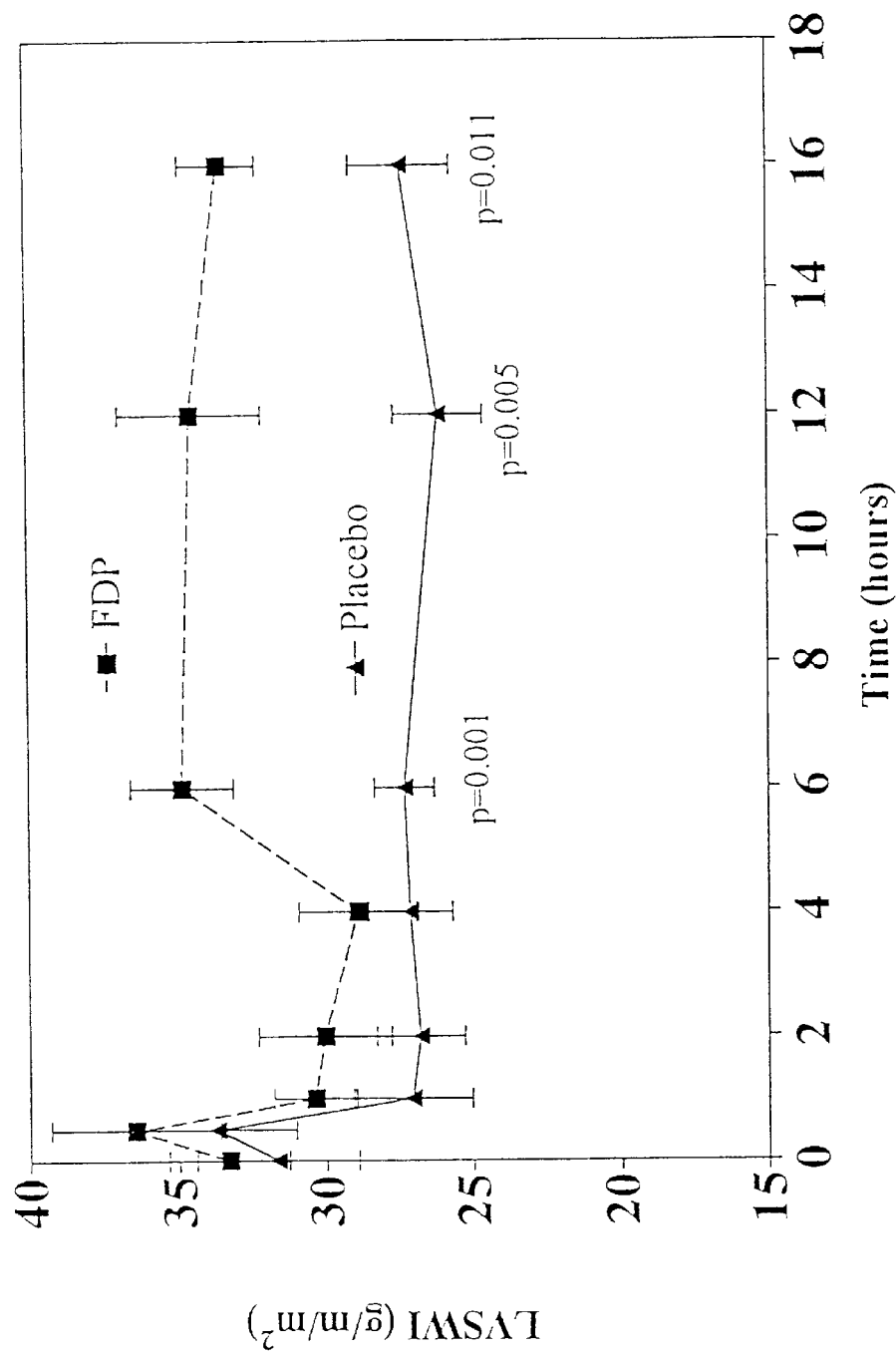

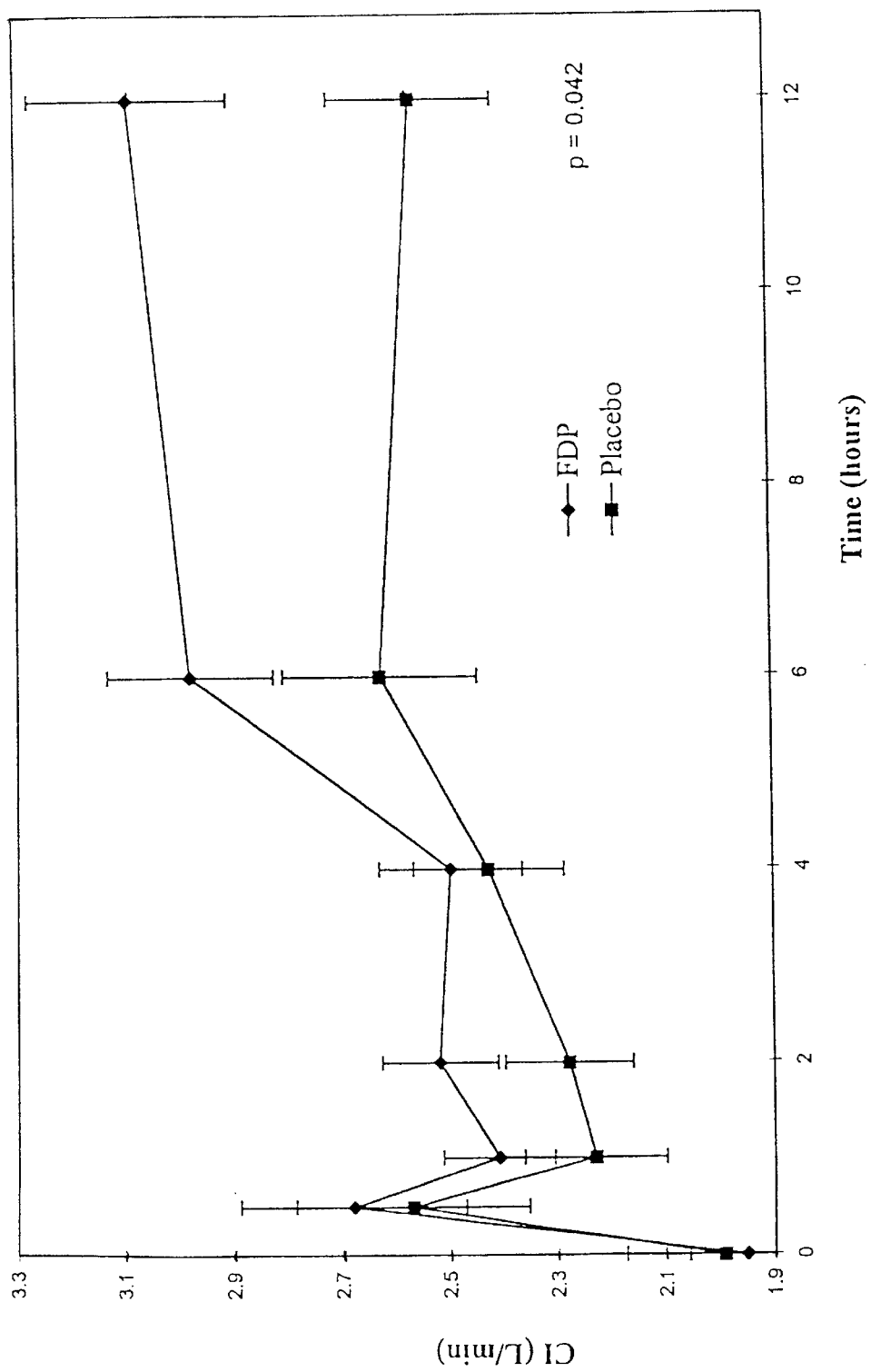

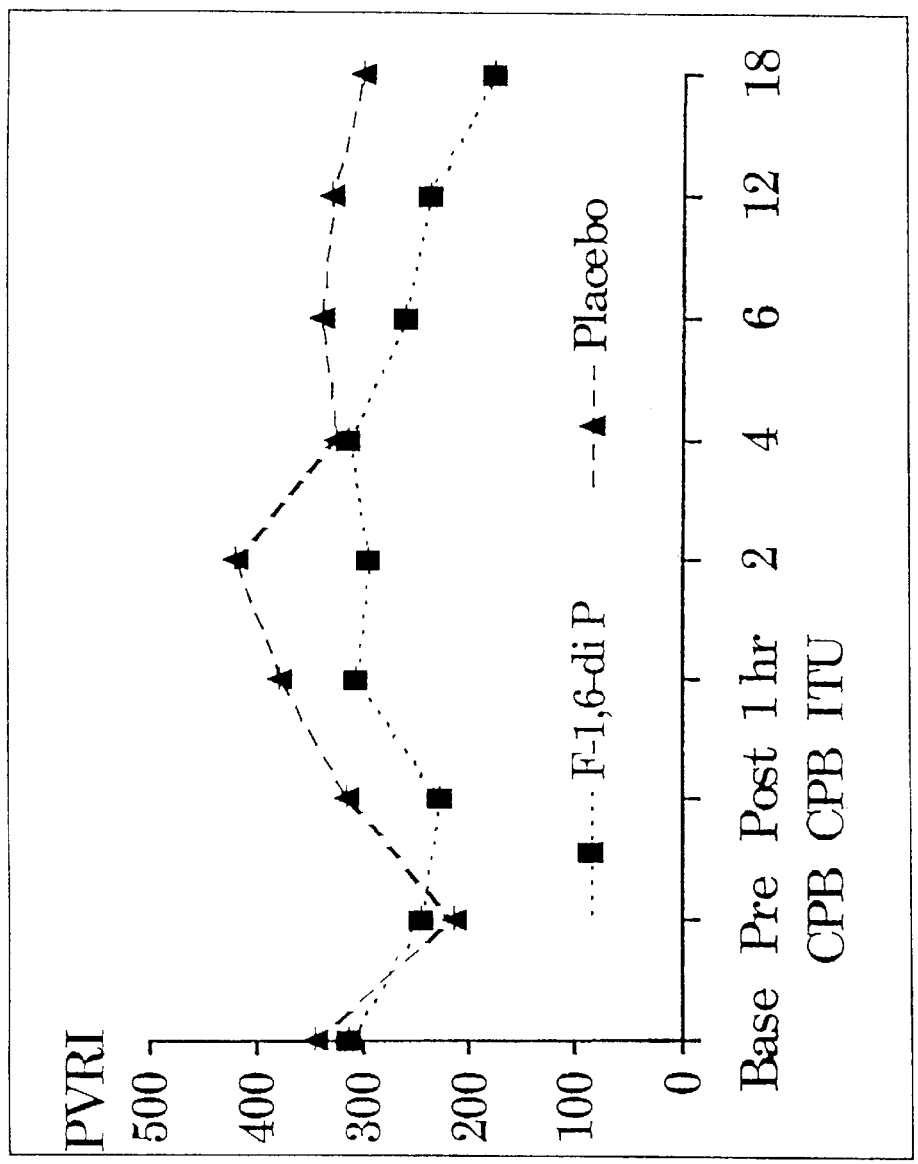

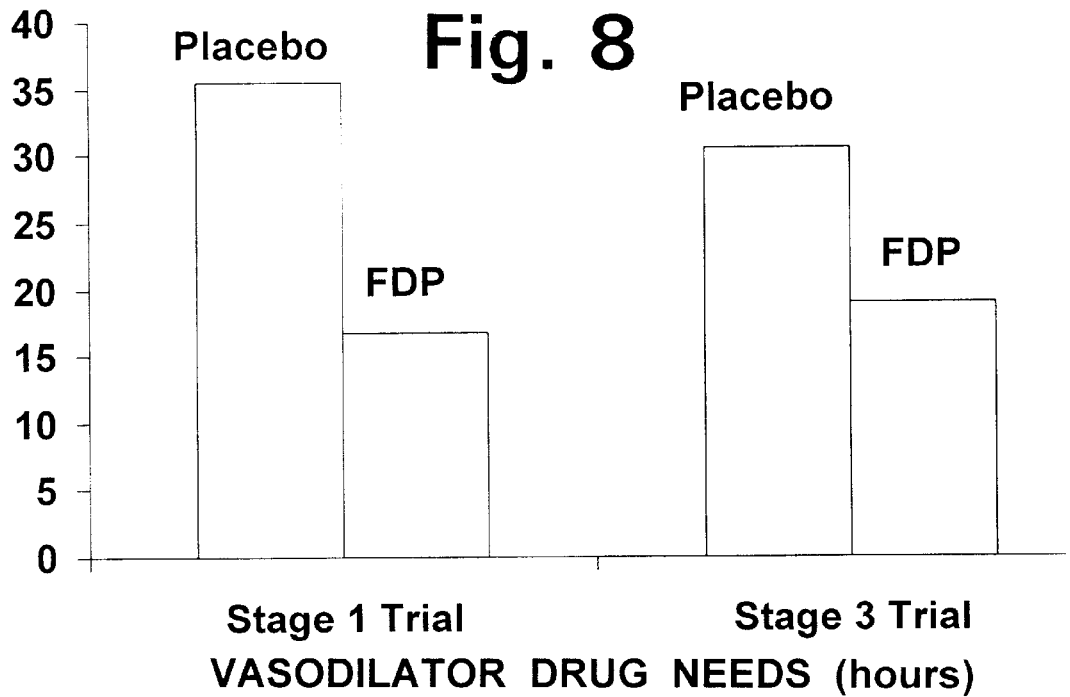
Fig. 8 VASODILATOR DRUG NEEDS (hours)
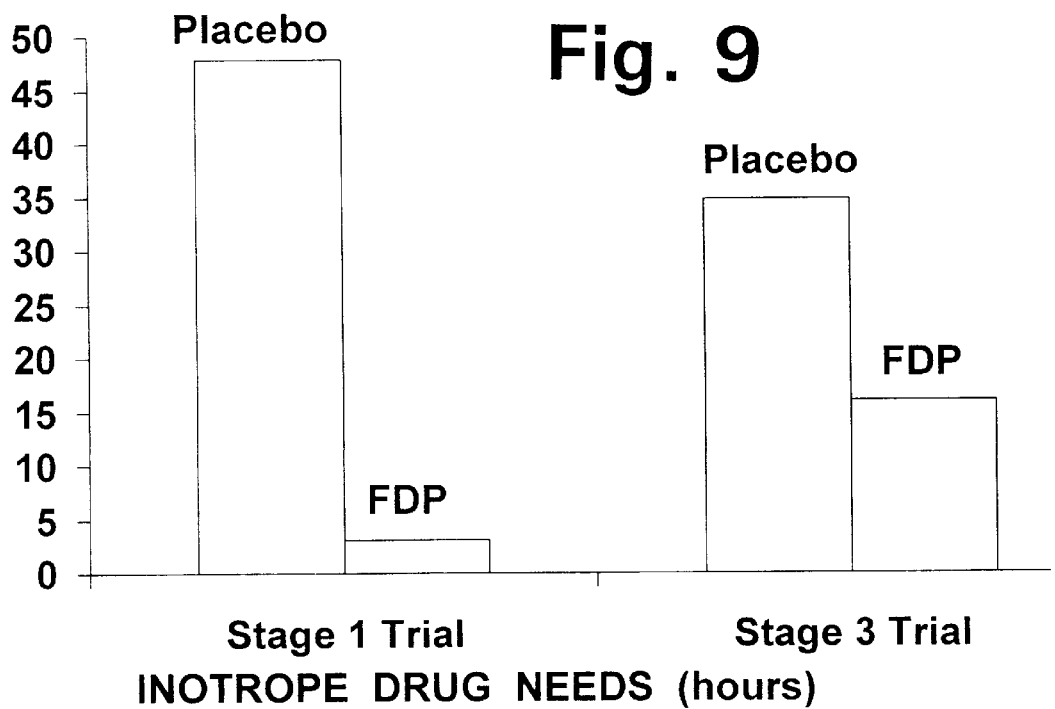
Fig. 9 INOTROPE DRUG NEEDS (hours)

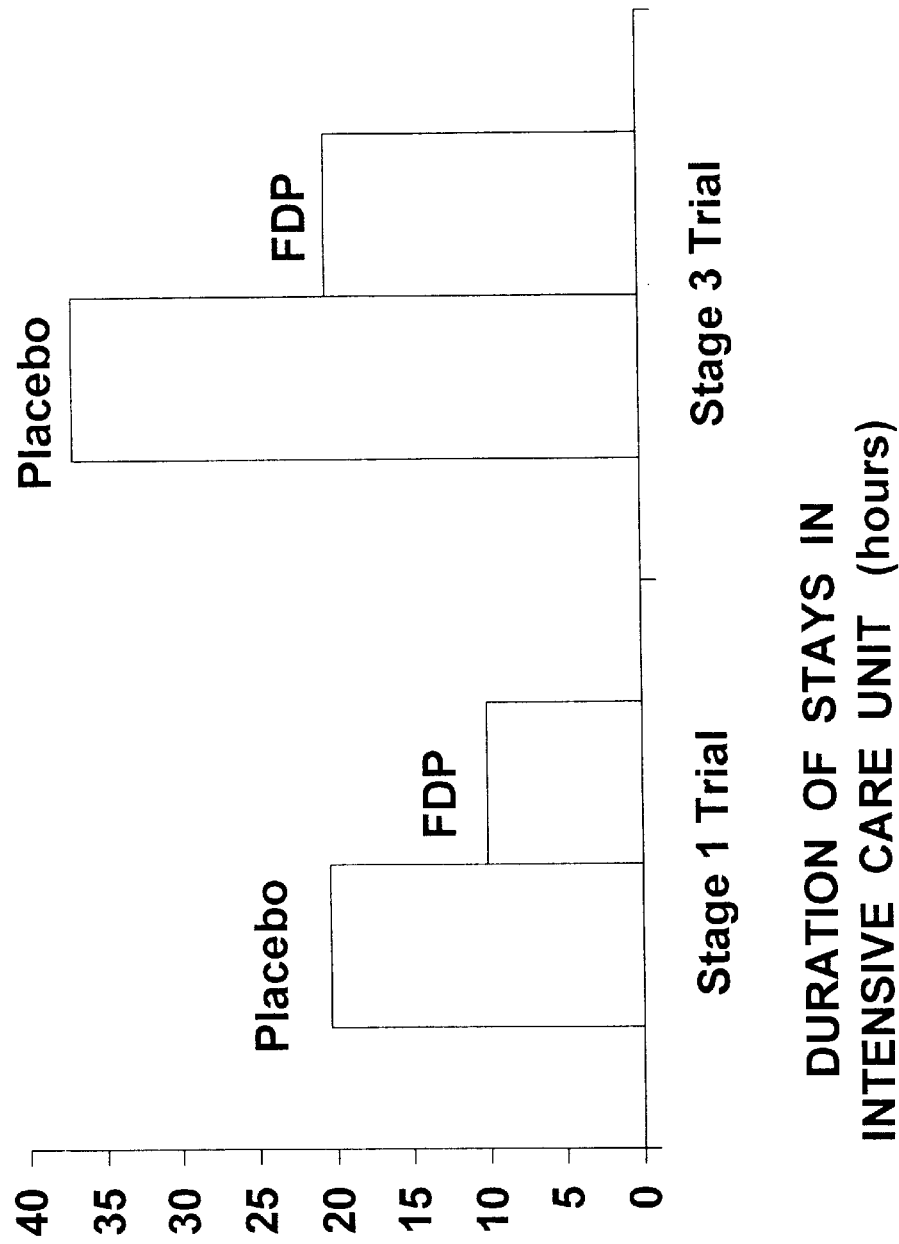

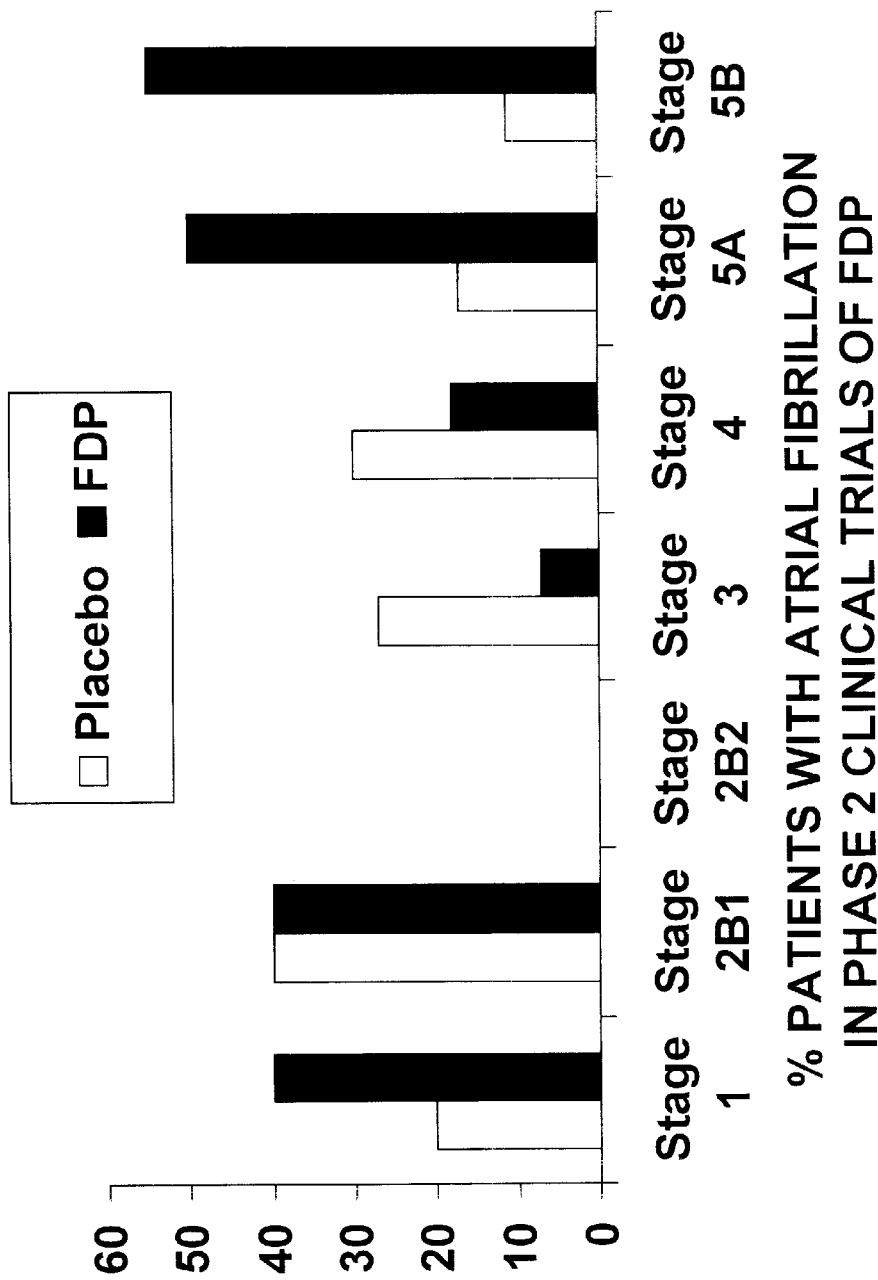

METHOD OF REDUCING PULMONARY HYPERTENSION AND ATRIAL FIBRILLATION AFTER SURGERY USING CARDIOPULMONARY BYPASS

BACKGROUND OF INVENTION

This invention relates to a method of using a drug to reduce and prevent two very serious problems that often arise as a result of surgery involving cardiopulmonary bypass.

As indicated by the name, "cardiopulmonary bypass" (abbreviated as CPB, and also referred to herein simply as "bypass") involves circulatory bypass of the heart and the lungs, during certain types of surgery. CPB is most commonly used in the following types of surgery:

(1) surgery to repair occluded (blocked or clogged) coronary arteries which cannot be adequately reopened by less invasive techniques such as balloon angioplasty; this type of surgery is often referred to as "coronary artery bypass grafting" (CABG) surgery;

(2) repair of heart valves (as used herein, this phrase includes replacing a native heart valve with a replacement valve, which can be completely mechanical or which may contain tissue, such as heart valves harvested from pigs or human cadavers and treated to reduce their antigenicity);

(3) surgical correction of cardiac arrhythmias, such as surgery to remove or ablate (using microwave radiation or other forms of treatment) segments of heart tissue that create "short circuits" that cause or aggravate irregularities in the heartbeat;

(4) removal of heart muscle tissue to increase contact between a ventricular wall and oxygenated blood, as has recently been developed using laser devices;

(5) heart transplant surgery;

(6) lung transplant surgery; and, (7) surgery to correct a congenital heart disease, which is done most commonly in children. It should be noted that children who suffer from congenital heart disease that is sufficiently severe to require CPB surgery also tend to suffer from high rates of pulmonary hypertension.

All of these types of surgery are described in various well-known medical texts, such as *Gibbon's Surgery of the Chest* (Sabiston and Spencer, eds., Saunders Publ., Philadelphia, Pa.) and in various medical journals that are devoted to the subject of cardiac and/or thoracic surgery.

During surgery that involves CPB, the heart is usually stopped from beating while it and/or the lungs are being worked on. The most common and obvious reason for temporarily stopping the heart is so that the surgeons will not have to perform delicate surgery on a "moving target". Normally, the heartbeat is stopped by the combined effects of 3 steps: (1) perfusing the heart with a liquid called "cardioplegia" solution, which contains a sufficient quantity of potassium to interfere with the cellular electrochemical interactions that initiate and control each heart contraction; (2) chilling the heart, by means such as pouring ice-cold saline slush directly onto it and allowing the cold slush to remain in contact with the heart, in a basin that is formed when the pericardial sac is cut open to expose the heart; and (3) clamping the aorta shut, so that the left ventricle cannot pump blood anywhere.

While the heart is not beating, most of the patient's body (excluding the heart and, to some extent, the lungs) are supported by a bypass machine (also called a CPB machine, or a heart-lung machine). This machine receives deoxygenated blood from the patient's body, adds oxygen and various nutrients to the blood, and pumps the oxygenated blood back into the patient's body, excluding the heart.

During bypass, the body and brain are cooled several degrees, to reduce the need of brain cells and other cells for oxygen and nutrients. The heart muscle must be chilled to a substantially colder temperature, since (in most operations) the heart receives no oxygenated blood whatever from the bypass machine.

While a patient is on bypass, the heart suffers from a condition called "ischemia". Ischemia refers to inadequate blood supply to an organ, or a portion thereof. Since blood is the only source of oxygen and nutrients for cells and tissue, ischemia imposes a major stress on cells and tissues. This is especially true for the heart and brain, which are much more vulnerable to ischemic damage than any other organs, because of various physiological factors. If ischemia persists in either of these organs for more than a few minutes without chilling the organ, severe metabolic derangement can begin to occur, and it can lead quickly to large-scale cell death, and to tissue death ("infarction") which can rapidly become lethal to the patient.

In addition, it should also be noted that when a ischemic organ's blood supply is re-established, the damage in the organ often increases, due to the formation of "free radical" compounds, catalyzed by enzymes such as xanthin oxidase. These highly reactive molecules will attack nearly any type of biomolecule, and can severely damage and rupture cell membranes in ischemic tissue shortly after it is resupplied with oxygen.

After the surgical work requiring bypass is completed, the surgeons flush out the potassium-containing cardioplegia liquid from the heart, and rewarm the heart muscle by passing warm blood or other liquid through the coronary arteries and veins. As the heart warms up, it usually begins to fibrillate, and the surgeons use electrodes to defibrillate the heart and restart the heartbeat.

When surgeons try to restart the heart after a period of bypass, the ischemic insult/damage to the heart muscle may be manifested in various ways. In almost all cases, at least some aberrations (including cardiac arrhythmias, abnormally rapid or slow heartbeat, ventricular fibrillation, or diminished pumping capacity) are likely to arise in varying degrees. These aberrations in heart performance, triggered by the ischemic and surgical insults to the heart, can trigger various complex interactions with and within the heart tissue that is still trying to recover from the ischemic period, in ways that tend to further complicate and aggravate hemodynamic (blood circulation) insufficiency during the period shortly after surgery.

To help understand the very complex challenge facing patients and surgeons involved in these procedures, it should be kept in mind that open-chest surgery is not done on healthy and vigorous patients with enough reserve capacity to help them withstand a major assault. Instead, it is almost always done on badly-weakened patients who have been struggling with serious heart problems for years, and whose health has slowly deteriorated to a point where they can no longer lead even a semblance of normal life without a major, life-threatening surgical intervention.

With proper care, the cardiac pumping aberrations that usually arise when the heart is restarted after bypass usually diminish within a few hours or days, as the patient gradually recovers from the operation. Nevertheless, these abnormalities are themselves a form of stress, and they make it more difficult and time-consuming for a patient who has been through CPB surgery to fully recover. In addition, these aberrations never completely disappear in some patients. Those patients must live with such problems, as both a symptom and a source of stress on their hearts, for the rest of their lives, which are often seriously degraded and shortened by the lasting and lingering damage to their heart's ability to function and pump blood normally and properly.

In addition, in a substantial fraction of CPB operations, the heart fails to begin beating properly in response to normal stimuli, while the chest remains open and the patient is still on the operating table. This type of crisis immediately becomes an all-out emergency, and the surgeons must rapidly resort to more powerful (and potentially damaging) stimulant drugs, and to electrical stimulation of the heart using higher voltages. In some cases, temporary implantation of a left-ventricle assisting pump or an aortic balloon pump becomes necessary; either of these can help handle some of the pumping load while the heart tries to recover some of its strength, but such devices are accompanied by other problems.

These emergency measures, if required to overcome a life-threatening crisis, impose even more stress on the patient's heart and body, and if these measures don't succeed quickly, the patient may die or suffer severe and permanent brain damage, comparable to a massive stroke.

STANDARD MEASURES OF HEART DAMAGE AND RECOVERY

There are various ways to measure the condition and performance of the heart, using mechanical pumping performance ("hemodynamic") criteria, as well as biochemical criteria involving blood chemistry. These values include:
1. "cardiac output" (abbreviated as CO), which measures how many liters of blood are pumped by the heart per minute.
2. "cardiac index" (CI), which is cardiac output (liters of blood pumped per minute), divided by the body surface area of the patient, to make these values more comparable between patients of varying sizes and weights.
3. "left ventricular stroke work index" (LVSWI), which measures how much pumping work a left ventricle does during each heartbeat. This quantity is divided by the surface area of a patient's body, to make LVSWI values comparable between patients of varying sizes and weights.
4. "pulmonary artery wedge pressure" (PAWP) values. If these values increase to abnormal levels, they indicate that the left side of the heart is unable to function properly.

All of these values (and other hemodynamic measurements) can be measured as described in various books and articles, such as pages 319–339 of Grossman and Baim 1991.

In addition to these hemodynamic measurements, damage to the heart can also be measured by using creatine kinase (CK), a large enzyme that cannot permeate out of a cell while the cell is alive. Heart cells contain a dominant version of this enzyme, usually designated as the CK-MB isozyme. Since this enzyme cannot escape from heart cells that are still living and viable, the concentration of CK-MB that has entered the circulating blood of a cardiac patient indicates the extent of heart cell death and permanent tissue damage in that patient, and helps distinguish between temporary symptoms (such as angina) and permanent damage.

Still other ways of evaluating treatments for CPB patients are known, including: (1) measuring how long patients had to remain in an intensive care unit (ICU) following the surgery, before they could be transferred to ordinary hospital rooms; (2) measuring how long an inotropic drug (which temporarily increases the strength of the heartbeat but which also causes dangerous side effects in already-weakened hearts) had to be used to stimulate the hearts of patients, after the surgery; and, (3) measuring how long a vasodilator drug (which dilates blood vessels) had to be used to stabilize patients, after surgery.

All of these indicators listed above were evaluated in double-blinded clinical trials on human patients undergoing CPB surgery (in specific, the surgery involved coronary artery bypass grafting). The resulting data, shown in the various figures herein and described in more detail in the examples, clearly showed that a drug called fructose-1,6-diphosphate (abbreviated as FDP, and discussed in more detail below), if administered in a proper dosage and manner, caused substantial improvements in all of the above-listed measures of heart performance, and helped speed up and improve the recovery of FDP-treated patients, following CPB surgery.

However, those findings were not the truly unexpected findings which form the basis of this current invention. Instead, this invention is based on the discovery that FDP, if administered in a certain dosage and in a certain manner to patients who are being prepared for CPB surgery, can substantially reduce and in many cases prevent two very important problems that, prior to this discovery, posed extremely difficult and intractable challenges and obstacles that prevented satisfactory recovery by a substantial portion of patients undergoing surgery that requires CPB.

Those two problems involve atrial fibrillation, and pulmonary vascular resistance. Each is discussed below, under its own heading.

ATRIAL FIBRILLATION

In addition to various types of cardiac aberrations (such as abnormally rapid or slow heartbeats, arrhythmias, etc.) that transiently occur in nearly all CPB surgery patients as their hearts are being restarted after bypass, a substantial fraction (usually about 30%) of patients who have chronic heart problems severe enough to require open-chest surgery suffer one or more episodes of atrial fibrillation (hereafter referred to as "A-fib") within several days after surgery.

A-fib is substantially different from ventricular fibrillation; in V-fib, either or both of the ventricular pumping chambers ceases to pump blood, thereby causing complete cardiac arrest, which can kill a patient within a few minutes. By contrast, A-fib does not rise to the level of an immediately life-threatening crisis.

Nevertheless, if A-fib occurs, it is a serious and potentially very dangerous event, for a number of reasons which include: (1) it disrupts and interferes with proper blood flow and transport through the heart, thereby impeding the ability of an already-weakened heart to adequately supply the body with blood; (2) the much-too-frequent and badly uncoordinated electrical impulses that can be emitted by affected atrial tissue can trigger and provoke irregularities in adjacent ventricular tissue, leading to potentially serious ventricular pumping problems such as bradycardia, tachycardia, and arrhythmias; and, (3) because an atrial chamber is not contracting properly, it poses a serious risk of blood stasis inside the affected atrial chamber. In other words, a small quantity of blood may become effectively trapped and completely stationary, in some corner, pocket, or recess inside the atrial chamber.

If blood stasis occurs as a result of A-fib, the non-moving pocket of blood may form a major blood clot, which poses a major threat of becoming dislodged and travelling to the lungs or brain, leading to a major life-threatening stroke or pulmonary embolism. To prevent this type of life-threatening risk from atrial fibrillation, people who suffer from A-fib must be put on an anti-coagulant drug. However, such drugs create their own problems and adverse side effects; among other things, they can delay and retard the ability of the body to repair itself from the cutting and suturing required by the surgery.

Accordingly, even a single episode of A-fib following CPB surgery is a very important event, which requires the patient to be placed on anti-coagulant drugs, and which also means that the patient will require more extensive and careful monitoring, during recovery from surgery. A single episode of A-fib following CPB surgery usually extends the length of the hospital stay for that patient by at least 3 days, and quite often up to 5 days longer than normal, and requires higher levels of monitoring and medical attention while the patient remains in the hospital. Because of the high costs of this type of intensified care in a hospital, a single episode of A-fib following CPB surgery usually increases the cost of a patient's hospital stay by at least $10,000, on average.

Accordingly, atrial fibrillation is a very important factor (also called an "end point" for purposes of statistical analysis) for evaluating the safety and efficacy of any potential drug that might be useful for treating patients who undergo surgery that requires cardiopulmonary bypass.

Atrial fibrillation requires and deserves special attention herein, because it has been discovered, through clinical trials on humans, that the rates and risks of A-fib after CPB surgery reveal an apparently major dividing line between two totally different things. First, certain methods of using FDP before and during CPB surgery have been shown to be safe, effective, and highly beneficial in substantially reducing the risk of atrial fibrillation after surgery. But second, other unsafe methods of using FDP in CPB surgery can have the opposite effect, and apparently can substantially increase the risks and occurrence rates of atrial fibrillation after CPB surgery.

Accordingly, the invention disclosed herein relates to a method for intravenously injecting FDP into patients in a dosage and a manner (involving factors such as the timing of injections, and the possible co-administration of one or more additional active agents along with the FDP, to counteract a specific danger posed by the FDP) that reduces the risks and occurrence rates of A-fib, after CPB surgery. By contrast, as also discovered and discussed herein, if FDP is administered at an unsafe dosage and manner, the risk of A-fib will be substantially increased rather than reduced.

In brief, the data obtained to date from human clinical trials indicates that if FDP is administered in a manner that avoids a substantial accumulation of excess lactic acid (which is one of the main chemical byproducts of administering FDP under oxygen-deficient conditions), the FDP can substantially decrease the risks and occurrence rates of atrial fibrillation. However, if FDP is administered in a dosage and manner that causes or aggravates lactic acidosis, the risks and rates of atrial fibrillation increase, rather than decrease.

PVR AND PULMONARY HYPERTENSION

Another very important factor in CPB surgery involves blood flow through the lungs. This blood flow is directly affected by a parameter called "pulmonary vascular resistance" (PVR), which measures the drop in blood pressure between a pulmonary vein (exiting the lungs) and a pulmonary artery (entering the lungs). This drop in blood pressure is caused by the resistance to fluid flow through blood vessels (mainly capillaries) inside the lungs. High levels of vascular resistance (also called "pulmonary hypertension") indicate that blood is not flowing properly through the lungs, due to problems such as edema, inflammation due to an allergic response, immune response, histamines or cytokines, or other forms of tissue stress or damage inside the lungs.

Since it measures a drop in pressure, PVR can be expressed in metric terms (dynes-second/cm$^3$), or in terms of millimeters of mercury column. It can also be expressed as a PVR Index (PVRI), in a manner comparable to cardiac index, by dividing a PVR value (the metric version) by the surface area of the body of a patient, to give values in dynes-second/cm$^5$.

Pulmonary hypertension following CPB surgery is an extremely difficult and often intractable problem to treat, since it usually does not respond adequately to conventional treatments (such as vasodilators and inotropic drugs) that can be used to control elevated vascular resistance in the rest of the body. Because it cannot be controlled adequately by conventional drugs, pulmonary hypertension is a very common and very important contributing factor in deaths following cardiopulmonary bypass surgery; indeed, in almost all deaths that follow shortly after CPB surgery, where a patient never fully recovered from the surgery, pulmonary hypertension is almost always involved as one of the main causes of death.

This is largely due to the fact that pulmonary hypertension imposes its entire resistive load against the right ventricle of the heart. The right ventricle only pumps blood through the lungs, so it is substantially smaller and less powerful than the left ventricle, which supplies blood to the entire remainder of the body. While the left ventricle is well-adapted to cope with transient increases in pumping loads, such as caused by exercise and other physical exertions, the right ventricle is not well adapted to handling those types of increased pumping loads. Since pulmonary hypertension following CPB surgery can impose a heavily-increased load on a portion of the heart that is not well-adapted to coping with extra-heavy loads, it is one of the most difficult and dangerous problems that can arise after such surgery.

The results of the tests disclosed herein indicated that FDP treatment in proper dosages and at proper times, before and during CPB surgery, caused an important and very useful benefit, by substantially reducing the increases in PVR levels that normally occur during and immediately following CPB surgery. These results are described in more detail below.

Since elevated PVR levels after CPB surgery are so difficult to treat effectively using any other known drugs, the discovery that FDP, if injected in properly quantities and a proper manner before and during CPB surgery, can effectively control and prevent large and dangerous increases in PVR levels, offers a potentially major breakthrough in treating a problem that previously has been one of the most difficult, dangerous, and intractable problems in CPB surgery.

FAILED PRIOR EFFORTS TO EFFECTIVELY TREAT CABG PATIENTS

Despite the best efforts of thousands of cardiac surgeons and other researchers who have been working for decades to solve or minimize the problems that inevitably accompany open-chest cardiac surgery, many patients who undergo surgery that requires CPB often suffer substantial (and in many cases severe) damage to their heart muscle and tissue, due to the surgery.

Since surgery that requires CPB (including CABG surgery, surgery to repair heart valves, etc.) is so common, this is a major medical problem. It has been known about and closely studied for decades, but it has not yet been solved.

The problems of limited and inadequate progress in this field of research are rendered even worse by the fact that tests using lab animals or cell or tissue cultures have been poor and inadequate predictors of success, in numerous methods that have been proposed to improve the outcomes of cardiac surgery in human patients. Table 1 lists a number of drugs which showed good promise for potential use during cardiac surgery, based on in vitro tests (i.e., cell culture tests, as well as tests on intact hearts that had been removed from sacrificed lab animals and kept beating by mechanical support equipment), and on in vivo tests using intact living lab animals. Regrettably, none of those drugs proved to be useful, in human clinical trials.

As shown by that table and the articles cited therein, research in this field has been very active, but it has been littered with failed efforts to improve the outcomes of a type of surgery that is done hundreds of thousands of times, every year. If there were any obvious answers to the daunting task of improving the outcomes of cardiac surgery, cardiac surgeons would quickly embrace and use those answers. The fact is, there are no such answers which are "obvious" to the surgeons who actually do this type of surgery.

BACKGROUND ON FRUCTOSE-1,6-DIPHOSPHATE (FDP)

The treatment described herein involves a sugar-phosphate molecule called fructose-1,6-diphosphate (abbreviated as FDP). Some articles refer to this molecule as fructose-1,6-biphosphate, or as fructose-1,6-bisphosphate.

Any references herein to FDP or fructose diphosphate refer only to the 1,6-isomer of fructose diphosphate, with phosphate groups bonded to the #1 and #6 carbon atoms of the fructose molecule. Other isomers (such as fructose-2,6-diphosphate) also occur, but they are of no interest herein.

FDP (the 1,6-isomer) is a naturally occurring molecule which is created and then quickly consumed during a series of chemical reactions inside cells called glycolysis. Since FDP

TABLE 1

EXAMPLES OF DRUGS THAT SHOWED PROMISING RESULTS IN CELL CULTURE OR ANIMAL TESTS, BUT CANNOT EFFECTIVELY PROTECT CARDIAC MUSCLE IN HUMANS

| Class of agent | Example references | Outcome in Human tests |
|---|---|---|
| Superoxidase (SOD) mimetics | Werns et al (1988) J Cardiovasc Pharmacol 11:36–44 | FAILED |
| Acadescine | Menasch et al (1995) J Thor Cardiovasc Surg 110:1096–1106 | FAILED |
| Adenosine | Fremes et al (1995) J Thor Cardiovasc Surg 110:293–301 | FAILED |
| Polyethylene-glycol-SOD | Omar et al (1991) J Mol Cell Cardiol 23:149–159 | FAILED |
| β-adrenergic blocking drugs | Lu et al (1989) Arch Int Pharmacodyn Ther 301:165–181 | FAILED |
| Calcium channel blocking drugs | Watts et al (1986) J Mol Cell Cardiol 20:443–456 | FAILED |
| PAF antagonists (e.g., Ginkolide B) | Koltai et al (1989) Eur J Pharmacol 164:293–302 | FAILED |

TABLE 1-continued

EXAMPLES OF DRUGS THAT SHOWED PROMISING RESULTS IN CELL CULTURE OR ANIMAL TESTS, BUT CANNOT EFFECTIVELY PROTECT CARDIAC MUSCLE IN HUMANS

| Class of agent | Example references | Outcome in Human tests |
|---|---|---|
| FR76830 | Ishibashi et al (1991) Cardiovasc Res 24:1008–1012 | FAILED |
| Nitrobenzyl-thioinosine | Kuzmin et al (1989) Fiziol Zh 35:3–9 | FAILED |
| Nitroglycerine | Feng (1996) Int J Cardiol 55:265–270. | FAILED |
| Pyruvate | Crestanello et al (1995) J Surg Res 59:198–204 | FAILED | is a short-lived intermediate that is quickly consumed by subsequent reactions, it normally is present in cells only at relatively low concentrations.

Glycolysis is a fundamental biological process that is essential to the generation and use of energy by cells; briefly, it is the process by which glucose, a sugar molecule, is chemically broken apart, to release energy.

In a first set of reactions, which can occur without requiring any oxygen, a molecule of glucose (with 6 carbon atoms) is broken apart to form two molecules of pyruvate, with 3 carbon atoms. These reactions are called the Embden-Meyerhof pathway, and they yield a relatively small amount of ATP (adenosine triphosphate, a high-energy metabolite that is then used to drive other chemical reactions).

Subsequently, either of two things can happen to pyruvate molecules that are formed by splitting apart glucose. If enough oxygen is present in the cells, pyruvate will be oxidized all the way to carbon dioxide and water, in a set of reactions called the Krebs pathway, or the "aerobic" pathway. These reactions release a great deal of energy. However, if not enough oxygen is present in a cell (as occurs under conditions of ischemia, where the blood supply to the tissue has been disrupted), the pyruvate molecules (with 3 carbon atoms) are merely rearranged to form lactic acid, which also contains 3 carbon atoms. This reaction generates no ATP.

Glycolysis is discussed in numerous texts on biochemistry, physiology, or cell biology. For example, any edition of Stryer's Biochemistry, Lehninger's *Biochemistry*, Guyton's *Medical Physiology*, or Alberts et al, *Molecular Biology of the Cell* contains a fairly extensive analysis of glycolysis.

FDP stands at the absolute peak of the energy curve that can be used to show the progress of glycolysis through its various intermediates, starting with glucose and leading to pyruvate. Two molecules of ATP must be consumed, in order to get the process completely primed by "boosting" glucose up to an even higher level of energy contained in FDP. After the peak energy level of the FDP intermediate is reached, the subsequent reactions begin to release that energy stored in the FDP.

Since researchers have known for decades that FDP stands at the very highest peak of the energy curve in glycolysis, numerous researchers have wondered and speculated for decades about whether FDP might be useful, as a drug, to help temporarily boost energy supplies in the cells or tissue of patients suffering from ischemic crises or other problems of ischemia or hypoxia. Any number of scientific articles and patents have been published, suggesting that FDP might be able to reduce cell death and tissue damage, if administered to patients suffering from ischemia or hypoxia. Examples of such articles, which stretch back to at least 1980, include Markov et al 1980, 1986, and 1987, Brunswick et al 1982, Granot et al 1985, Farias et al 1986, Grandi et al 1988, Zhang et al 1988, Cacioli et al 1988, and Lazzarino et al 1989 and 1992. These are just a few examples, and numerous other similar articles are also available. Relevant U.S. patents include U.S. Pat. Nos. 4,546,095 (Markov 1985), 4,703,040 (Markov 1987), and 4,757,052 (Markov 1988).

However, despite these numerous articles and patents stretching back two decades, FDP simply is not used by surgeons to treat patients who are undergoing cardiac surgery, even though every surgeon in the world is well aware of the need for ways to reduce the ischemic stress and damage that is inflicted on hearts during surgery that requires cardiopulmonary bypass.

Indeed, FDP is not used or prescribed by physicians or surgeons for any medical purposes at all, except for a few researchers who are carrying out small-scale clinical trials, none of which (to the best of the Applicant's knowledge and belief) involve cardiopulmonary bypass surgery, except for the tests described below, which were sponsored and funded by the assignee and applicant, Cypros Pharmaceutical Corporation.

In point of fact, medical-grade FDP (i.e., FDP in a form that is suitable for injection into humans, as distinct from the non-sterile chemical, which is available in bulk but which would be completely unsuited and illegal for injection into humans) is not even available in the United States, or in any other industrialized nation with the possible exceptions of Italy and China. Except possibly in Italy and/or China, it cannot be purchased and used on human patients by physicians or surgeons at all, unless the physicians or surgeons go to the extraordinary trouble of developing an entire research project involving FDP as an experimental drug. Any such research project would need to be individually approved as a form of experimentation, rather than treatment, by institutional review boards as well as the federal Food and Drug Administration.

This is the actual and current medical status of FDP. It simply is not used today for CPB surgery, or for any other type of surgery or medical treatment, except in a few small clinical trials, which are experimental research rather than a recognized form of medical treatment.

The failure or refusal of surgeons to use FDP on patients who are preparing to undergo CPB surgery is believed to be mainly due to at least two major and hugely important factors.

The first major factor which teaches away from the use of FDP to treat CPB surgery patients is this: since FDP is a diphosphate with a strong negative charge, it is widely assumed by doctors and researchers that it will not enter cells in significant quantities. Since glycolysis occurs solely inside cells, reports which openly state that FDP will not reach cell interiors in significant quantities would appear to pose a major and unavoidable barrier to the successful medical use of FDP. As one example, Pasque et al 1984, a review article, offers a detailed analysis of the presumed and apparent shortcomings of FDP. It reviewed numerous drug strategies that had been proposed for increasing ATP levels in heart tissue, and then completely dismissed FDP as a potentially useful treatment. As stated by Pasque et al, "According to its proponents, [FDP] results in an enhanced rate of anaerobic glycolysis . . . there are arguments based on sound data to refute these claims. First, the likelihood of a phosphorylated compound, such as fructose 1,6-diphosphate, crossing the myocardial cell membrane intact is small. Second, the phosphofructokinase reaction, although thought to be rate limiting in normal myocardium, does not limit glycolysis in ischemic myocardium. Limitation instead occurs at the glyceraldehyde-phosphate dehydrogenase step, which is distal to the phosphofructokinase reaction in the glycolytic pathway. Finally, a lack of direct metabolic effect of fructose 1,6-diphosphate on the ischemic dog myocardium has been demonstrated with no evidence of myocardial ATP preservation or lactate elevation" (Pasque et al 1984, page 4).

Other articles which report essentially the same conclusions include Angelos et al 1993 (title: "FDP fails to limit early myocardial infarction size . . . ") Eddy et al 1995 (titled: "Lack of a direct metabolic effect of fructose, 1,6-diphosphate in ischemic myocardium") and Tortosa et al 1992 (title: "Fructose-1,6-bisphosphate fails to ameliorate delayed neuronal death . . .") All of these articles directly contradict the various hypotheses and proposals saying that FDP might be helpful in treating ischemia or hypoxia.

The second major factor which teaches directly away from the possible use of FDP, to treat patients suffering from ischemic or hypoxic crises, involves the fact that FDP, if metabolized by ischemic cells, leads to the production of lactic acid, which can inactivate a crucially important enzyme called phosphofructokinase (abbreviated as PFK).

In glycolysis, the PFK enzyme converts fructose monophosphate into fructose-1,6-diphosphate, by adding a phosphate group to the monophosphate compound. Because of how the glycolytic pathway evolved, the reaction which is catalyzed by the PFK enzyme became the limiting step that controls the overall rate of glycolysis. This limiting and controlling mechanism is absolutely essential to cells and tissue, because it prevents cells and tissue from burning up their energy supplies too rapidly.

Under conditions of ischemia or hypoxia, excess quantities of lactic acid can inhibit and even "poison" (irreversibly inactivate) the PFK enzyme. If PFK molecules are severely inhibited by accumulating lactic acid, it can create a crucially important bottleneck which can shut down the entire process of glycolysis in affected cells. Because the PFK-controlled step plays a crucial role in controlling and limiting energy generation by cells, inactivation of PFK by lactic acid can completely shut down subsequent glycolysis in ischemic cells, thereby stopping all energy production in those cells, and thereby causing the death of those affected cells and tissue.

Several other factors should also be recognized, in evaluating the obstacles that FDP would need to overcome in order to be useful in ischemic tissue.

First, only a small amount of energy is released under oxygen-starved conditions, when glucose (or an exogenous supply of FDP) is broken apart into pyruvate and the pyruvate is then converted into lactic acid. The energy yield of glycolysis under anaerobic conditions is only 47 kilocalories of energy per mole of glucose converted to lactic acid. By comparison, the energy yield of glycolysis under normal conditions, when oxygen is present, is almost 15 times greater (i.e., 686 kilocalories of energy per mole of glucose.

The fact that only very small quantities of useful energy will by released by converting glucose or FDP into lactic acid, under anaerobic conditions, is aggravated by the fact that large quantities of lactic acid will be generated from FDP, if the FDP can somehow enter ischemic cells. Lazzarino et al 1992 described a test where FDP was added to intact isolated hearts, which had been removed from sacrificed lab animals and which were being perfused on mechanical pumping equipment, using perfusion solutions that contained plenty of oxygen. Despite the fact that the perfusion fluid contained plenty of oxygen, only about 10% of the FDP was oxidized all the way to carbon dioxide and water. Nearly 90% of the FDP was converted into lactic acid, which, as noted above, poses a major risk of inhibiting or even shutting down glycolysis by inhibiting the crucial PFK enzyme.

Accordingly, researchers who understand the complexities of glycolysis (including (i) the large amount of lactic acid that is formed when FDP is metabolized under ischemic conditions; (ii) the small amount of useful energy that is generated when lactic acid is formed from glucose or from exogenous FDP; and (iii) the threat that excess lactic acid will inhibit or shut down the glycolysis-controlling PFK enzyme) would assume that the risks of injecting FDP into a patient suffering from an ischemic or hypoxic crisis are high, especially when compared to the small potential benefits, in terms of only low amounts of energy being released when lactic acid is formed from the FDP. Apparently, in the judgment of most researchers and surgeons during the past 20 years, the inability of FDP to enter intact cells, and the risk that exogenous FDP poses of suppressing or even shutting down glycolysis by leading to the generating of excess lactic acid, have outweighed their assessment of any potential benefits FDP might be able to offer, in patients undergoing surgery that requires cardiopulmonary bypass.

The fact that cardiac surgeons (who are acutely aware of the ischemic damage that arises in heart tissue during cardiopulmonary bypass surgery) have not chosen to use FDP, during their surgery on actual patients, directly contradicts and refutes any presumption or assertion that it would be "obvious to anyone with ordinary skill in the art" to use FDP on patients undergoing cardiac surgery. Little or no effort has ever been devoted by any pharmaceutical companies, other than the assignee company herein, to actually developing FDP as a drug, and making it available to doctors who would like to use it in human patients. Under the laws enforced by the U.S. Food and Drug Administration, FDP cannot be sold in the United States for administration to humans, by physicians. With possible minor exceptions in China and Italy, FDP simply is not being administered to patients, by physicians or surgeons, for any type of medical use, except for certain types of experimental testing in small-scale clinical trials.

PRIOR ART PREPARATIONS OF FDP

FDP is sold in bulk, as a non-sterile chemical, for non-medical uses, by chemical supply companies such as Boehringer-Mannheim, located in Germany. Such non-sterile bulk preparations are not intended, and not suited, for injection into humans, and are not included within the term "medical-grade FDP" as used herein.

Currently, the only known preparation of potentially medical-grade FDP which is commercially available anywhere in the world (other than research reagents sold in gram or milligram quantities by specialty chemical companies) is sold in Italy, by a company called Biochemica Foscama. However, the Biochemica Foscama preparation suffers from a number of substantial limitations. It is relatively inhomogeneous, and contains particles of varying different sizes; some appear to be small glass-like beads, while others appear to be relatively sticky, caramelized agglomerations. It is also relatively unstable; while pure FDP is a crystalline white powder, the Biochemica Foscama preparation (especially the beads and agglomerations) turns yellowish-brown within a few weeks, when stored at room temperature, unopened.

The manufacturing method used by Biochemica Foscama is not well-suited for the sterility requirements of human drugs, and the resulting preparation apparently does not have sufficient purity to qualify for sale and use as a human drug in the United States. Briefly, a large tray of a liquid mixture of FDP is frozen, then lyophilized, then ground up into a powder, which is then loaded into vials. It is effectively impossible to ensure sterility when this type of large equipment is used. In addition, FDP is chemically unstable; either of the phosphate groups can spontaneously break off from the molecule, leaving the monophosphate residue, which is effectively worthless. Therefore, a "terminal sterilization" step (such as pasteurizing, autoclaving, or irradiating the FDP after it has been loaded into the vials) cannot be used, because such steps would seriously degrade the resulting chemical.

The Biochemica Foscama company is aware of these shortcomings. However, it apparently has no intent to develop a different and improved manufacturing processes, in view of the general lack of interest in FDP among physicians and surgeons in industrialized nations.

Other dried FDP preparations have been made in Japan and China, as disclosed in U.S. Pat. No. 5,094,947 (issued in 1992 to Nakajima et al, based on a prior Japanese application) and Chinese patents 1,089,615; 1,089,616; and 1,089,654, invented by Ou-Yang et al). However, those research efforts apparently have not been developed further, and to the best of Applicant's knowledge and belief, no effort has been made by either of those Japanese or Chinese research teams to develop FDP as a commercial product, or to obtain approval to sell either of those preparations for use in human patients, either in Japan or China, or in the United States.

Despite the lack of interest in FDP among other drug companies, the assignee and applicant herein (Cypros Pharmaceutical Corporation, located in Carlsbad, Calif.) has invested millions of dollars in clinical trials, to evaluate FDP for use in treating several otherwise intractable medical problems, such as treating sickle cell anemia patients during sickling crises, and for reducing cardiac damage caused by CABG surgery.

In addition, Cypros has also invested a great deal of money and effort in developing a new, improved, and different method of manufacturing a highly pure and sterile form of FDP, which has sufficient chemical stability to provide a shelf life of months and possibly even years, without requiring refrigeration. Unlike any other prior efforts by any other company or researcher, this new method uses sterilizing and manufacturing techniques that are carefully selected and designed to create a completely sterile and stable formulation, in a sealed vial. This new manufacturing method is disclosed in detail in U.S. Pat. No. 5,731,291 (Sullivan and Marangos, 1998), the contents of which are hereby incorporated by reference. That patent is owned by the same Applicant and assignee company that owns this current application.

Accordingly, one object of this current invention is to disclose a method of treating patients who are about to undergo surgery that requires cardiopulmonary bypass (CPB). This method involves injecting FDP into such patients, while the heart is still beating before bypass begins, in a quantity that reduces the risks of atrial fibrillation during the recuperative period following the surgery. This method requires that the FDP be administered to such patients in a manner which avoids creating lactic acidosis in such patients, during the period immediately following surgery.

Another object of this invention is to disclose that when FDP is injected into patients who undergo CPB surgery, the risk of creating excess lactic acid accumulation and lactic acidosis can be reduced by co-administering, along with the FDP, either or both of the following: (i) a buffering or alkalizing agent, such as sodium bicarbonate; or a (ii) drug that inhibits the production of lactic acid from pyruvate, such as dichloroacetate.

Another object of this invention is to disclose that when FDP is injected into patients who undergo CPB surgery, while the heart is still beating before bypass begins, the FDP treatment can also reduce unwanted increases in pulmonary vascular resistance, and in many patients can help the patients completely avoid pulmonary hypertension, which previously has been extremely difficult to treat using known drugs.

These and other objects of the invention will become more apparent through the following summary, drawings, and description of the preferred embodiments.

SUMMARY OF THE INVENTION

A method is disclosed for using fructose-1,6-diphosphate (FDP) to treat, reduce, and prevent two very serious problems that often arise as a result of surgery involving cardiopulmonary bypass. Before bypass begins and before the heartbeat is stopped, a liquid that contains FDP is intravenously injected into the patient, preferably over a sustained period of time (such as about 10 to about 30 minutes) to allow the FDP to permeate in significant quantity into the heart and lungs while the heart is still beating. FDP preferably should also be added to the cardioplegia solution that is pumped through the heart to stop the heartbeat, and/or during bypass. This treatment was found to reduce two very important and serious problems that have unavoidably plagued CPB surgery in the past, which are: (1) elevated levels of pulmonary vascular resistance (PVR), which includes pulmonary hypertension; and (2) high occurrence rates for atrial fibrillation. Prior to this discovery, there has never been any satisfactory treatment which could reduce the severity and occurrence rates for these two major problems.

If desired, FDP also can be co-administered in this manner along with (1) a buffering or alkalizing agent that counteracts acidosis, such as sodium bicarbonate or THAM (tris (hydroxymethyl)aminomethane), and/or (2) a drug that reduces the formation of lactic acid, such as dichloroacetate.

BRIEF DESCRIPTION OF THE DRAWINGS

FIG. 1 shows that injection of FDP before cardiopulmonary bypass began caused a substantial reduction in creatine kinase (CK) levels in circulating blood plasma, measured on the first and second post-operative days, in Stage 1 tests.

FIG. 2 shows that injection of FDP before cardiopulmonary bypass began helped patients regain more normal left-side heart function, as measured by reduced elevations of pulmonary artery wedge pressure (PAWP) values on the first post-operative day, in Stage 1 tests.

FIG. 5 is a graph showing that, in the Stage 3 tests, FDP substantially increased the ability of hearts to do their pumping work, as measured by "left ventricular stroke work index" (LVSWI) values.

FIG. 6 is a graph showing that, in the Stage 3 tests, FDP substantially increased the "cardiac index" (CI) values in treated patients.

FIG. 7 is a graph showing that, in the Stage 3 tests, FDP substantially decreased "pulmonary vascular resistance" (PVR) index values in treated patients. This was completely unexpected, since PVR is generated inside the lungs, rather than in the heart.

FIG. 8 is a bar graph showing that, in the Stage 1 and Stage 3 tests, FDP treatment significantly reduced the time that patients had to remain in an intensive care unit (ICU) after CABG surgery, before they could be transferred to ordinary hospital rooms.

FIG. 9 is a bar graph showing that, in the Stage 1 and Stage 3 tests, FDP treatment significantly reduced the amount of dopamine (a potentially dangerous inotropic drug) that had to be used to stimulate the hearts of CABG patients after surgery.

FIG. 10 is a bar graph showing that, in the Stage 1 and Stage 3 tests, FDP treatment significantly reduced the amount of glyceryl trinitrate (GTN, a vasodilator drug) that had to be used to stabilize CABG patients after surgery.

FIG. 11 shows the occurrence rate for atrial fibrillation for the different stages of tests involving varying dosages of FDP. In the Stage 3 tests (in which FDP was injected pre-bypass and in cardioplegia solution) and Stage 4 tests (in which FDP was injected pre-bypass, at a reduced dosage), FDP treatment reduced the number of patients who suffered atrial fibrillation. By contrast, in the Stage 5 tests, in which FDP was administered both pre-bypass and after bypass, occurrence rates for atrial fibrillation increased.

DESCRIPTION OF THE PREFERRED EMBODIMENTS

Figure 3:
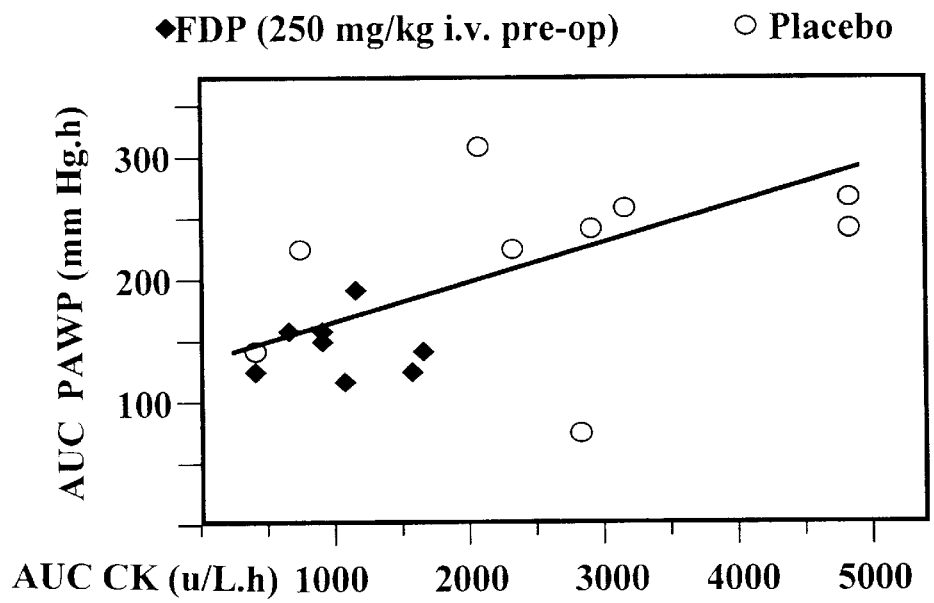
FIG. 3 is a graph of data from the Stage 1 tests, showing that the benefits of FDP injection into the heart muscle before cardiopulmonary bypass began, as shown biochemically by lower CK levels, also correlate with reduced abnormalities in hemodynamic pumping performance of the heart after CABG surgery. This confirms that FDP provided both biochemical and hemodynamic benefits, when infused into the heart before circulatory bypass begins.

This invention discloses a method of treating patients who are being prepared for surgery that requires cardiopulmonary bypass of the heart and lungs, by intravenously injecting or infusing a liquid that contains fructose-1,6-diphosphate (FDP) or a suitable salt thereof, such as a sodium salt, into such patients.

Unlike most previous articles involving the possible use of FDP for treating ischemic injury, which generally involve tests or trials in which FDP is injected after an ischemic injury or insult has already occurred or at least commenced, FDP treatment as disclosed herein must begin a sufficient period of time before cardiopulmonary bypass begins, to allow the FDP to permeate into the heart muscle and lung tissue before the heartbeat is stopped.

The clinical trials disclosed herein (referred to interchangeably as either trials or tests) were carried using a series of different dosage regimens, referred to herein as Stage 1 through Stage 5. The dosages used in each stage are briefly summarized in Table 2, along with a brief summary of the most important results of each stage, and are described in more detail below.

TABLE 2

FIVE "STAGES" OF CABG TESTING USING DIFFERENT FDP DOSAGE REGIMENS

| Designation | FDP Dosages | Summary of Outcomes |
|---|---|---|
| Stage 1 (n = 10) | 250 mg/kg pre-bypass, none in cardioplegia or post-bypass | Good reductions in blood CK and PAWP values No effect on Atr-fib rates |
| Stage 2 (n = 15) | 2.5 mM in cardioplegia - open label, cold, blood | No significant effects - baseline study, n = 5 in each of 3 subcategories |
| Stage 3 (n = 15) | 250 mg/kg pre-bypass and 2.5 mM in cardioplegia. None post-bypass | Good improvements in blood CK, PAWP, CI, CO, LVSWI Lower Atr-fib rates Lower pulm. vasc. resist. Lower drug needs & ICU time |
| Stage 4 (n = 10) | 125 mg/kg pre-bypass; none post-bypass | Minor trends (all good) in CK, PAWP, CI, LVSWI. No change in Atr-fib rates |
| Stage 5a (n = 6) | 250 mg/kg pre-bypass; 250 mg/kg at 2 & 6 hrs post-bypass | Measurable lactic acidosis Improved CK, PAWP, LVSUI BUT HIGHER ATR-FIB RATES |
| Stage 5b (n = 9) | 250 mg/kg pre-bypass; 125 mg/kg at 2 & 6 hrs post-bypass | Improved CK, PAWP, LVSWI BUT HIGHER ATR-FIB RATES |

In Table 2 (and below), all references to "pre-bypass" refer to injections that were carried out and completed before circulatory bypass of the heart and lungs began. References to "post-bypass" refer to injections that commenced after bypass had been terminated; for example, an injection "2 hours post-bypass" began 2 hours after the termination of bypass.

As used herein, "injection", "intravenous injection", and "infusion" are used interchangeably. Except for FDP that was added to cardioplegia solution, administration of FDP as disclosed herein normally used an infusion bag, which was coupled via a flexible tube to a hypodermic needle that had been inserted into an arm vein and then taped in place. This allowed the FDP to be infused into the circulating blood gradually, which is difficult when conventional syringes with needles are used. Injection of the FDP into a vein in the arm caused the injected FDP to be carried directly to the heart, without having to pass through any capillaries.

All divisions of patients into treatment vs. placebo groups were randomized, and controlled to ensure that no significant differences arose between treatment and placebo groups concerning gender, body weight, or age.

DOSAGES IN STAGES 1–5

As noted above and in Table 1, the tests disclosed herein were carried out in 5 sequential stages; before each stage commenced, the results from the prior stage tests were evaluated, and modifications were made if appropriate before the next stage commenced.

In general, these tests constitute what drug companies generally refer to as "Phase 2" clinical trials, using nomenclature that has been adopted by the U.S. Food and Drug Administration and various comparable foreign agencies. In general, Phase 1 tests usually evaluate the safety of various dosages of a candidate drug, in healthy people, to ensure that the drug can be administered safely (in subsequent Phase 2 tests) to people who actually have a disease or other medical problem. Since FDP is a completely natural compound that exists in all living cells, the U.S. FDA waived any requirements for Phase 1 tests for FDP. The various tests disclosed below all refer to Phase 2 tests, which are done on relatively small population samples, to develop a fairly detailed idea of what to expect, how the tests should be carried out in detail, and what dosages should be used.

If a drug performs well in Phase 2 tests, it becomes a candidate for even larger-scale Phase 3 tests which must be completed before a new drug can obtain full approval by the FDA for widespread sale and use, preferably using multiple different testing centers and using at least hundreds and preferably thousands of patients in both the treated and control populations, to further ensure that the results are entirely reliable and unbiased.

Accordingly, there is no pretense herein that the small sample sizes used in the tests described below are sufficient to merit consideration as Phase 3 tests. These were Phase 2 tests, and a full set of Phase 3 tests are currently being planned, which will use much larger populations of patients undergoing CABG surgery. Nevertheless, the results from the Phase 2 tests disclosed herein are sufficiently clear and strong to justify the conclusions and assertions set forth herein, based on actual human clinical trials using well-designed double-blinded testing procedures.

Stage 1 dosages used pre-bypass injection of 250 mg/kg FDP (i.e., 250 milligrams of FDP per kilogram of patient's body weight). The calculated amount (which differed slightly for different patients) was infused intravenously (IV) over a 20 minute span of time before cardiopulmonary bypass (CPB) began. This dosage was tested on 20 patients, divided into treatment and placebo groups having 10 patients each. This was a small number, but it was planned from the start that Stage 1 would be essentially a baseline test, to provide initial results so that subsequent tests with larger sample sizes could be planned intelligently based on the results of the first set of Stage 1 tests. As described below, subsequent Stage 4 tests used 125 mg/kg pre-bypass injections, to evaluate pre-bypass dosage without any complications from post-bypass injections. The results indicated that the 250 mg/kg was more helpful and beneficial to the patients, when post-bypass injections were not also administered.

It is believed that pre-bypass dosages in the range of about 150 to about 500 mg/kg (for whole-body intravenous injection) are likely to be safe and generally beneficial for most patients, with preferred dosages generally in the range of about 200 to about 400 mg/kg. Preferred dosages can be further evaluated and optimized by the methods disclosed herein using no more than routine experimentation, provided that careful attention is paid to lactic acid formation and blood pH in any such tests. As discussed in more detail below, pre-bypass dosages higher than 250 mg/kg can also be administered and evaluated in conjunction with a second agent that buffers or counteracts acid formation (such as sodium bicarbonate), or which reduces lactic acid formation (such as dichloroacetate).

Stage 2 used 2.5 millimolar (mM) FDP, added to the cardioplegia solution that was infused into the heart to stop the heartbeat. Certain minor differences were introduced in the Stage 2 tests, which resulted in subcategories that were designated as Stage 2a, Stage 2b1, and Stage 2b2. Stage 2a used non-blinded "open label" tests, in which the anesthesiologist knew whether or not FDP was in the cardioplegia solution; this was done as a precautionary measure on 5 patients, with no placebo controls, to make sure that FDP in the cardioplegia solution did not have any unanticipated adverse effects. Stage 2b1 used "cold cardioplegia", in which a chilled aqueous saline solution containing FDP (or a placebo), as well as potassium (5 mM) to help stop the heartbeat, was tested under double-blinded conditions. Stage 2b2 used "blood cardioplegia", in which the chilled cardioplegia solution also contained red blood cells which had been extracted from whole blood by centrifugation. Both subcategories used only 5 treatment patients and 5 control patients, since no significant effects were expected from FDP administered solely by cardioplegia (and no significant effects were observed).

Stage 3 used a combination of Stage 1 and Stage 2 dosages (i.e., 250 mg/kg pre-bypass dosage, from Stage 1, as well as 2.5 mM FDP in cardioplegia, from Stage 2). This regimen was tested on 30 patients (15 treatment, 15 placebo).

Stage 4 was intended to evaluate the pre-bypass dosage, and used 125 mg/kg, which was only half as much as the Stage 1 and Stage 3 tests. It also did not use any post-bypass injections. Although various factors trended in desirable directions (such as minor improvements in cardiac output, cardiac index, and LVSWI), these results were not as pronounced as the improvements seen in the Stage 3 tests. Accordingly, the 125 mg/kg pre-bypass dosage was regarded as mildly beneficial but non-optimal. All subsequent tests returned to the higher 250 mg/kg pre-bypass dosage, and the Stage 4 tests and results are not discussed in any further detail below.

Stage 5a, as used for the first 6 FDP-treated patients, involved 250 mg/kg pre-bypass, plus 250 mg/kg at 2 hours post-bypass, plus another 250 mg/kg at 6 hours post-bypass. This infusion of 750 mg/kg (which is almost 70 grams of FDP, for a patient weighing about 90 kg, which is about 200 pounds), over about a 7 hour period, caused significant levels of lactic acidosis. This dosage caused improvements in blood CK values, PAWP values, cardiac index, cardiac output, and LVSWI, all of which were beneficial. However, this dosage suffered from a major and highly important drawback: 3 of the 6 patients tested at this dosage of FDP suffered atrial fibrillation.

Despite the very small sample size and the unreliability of statistical analyses when studying such small populations, the 50% occurrence rate for a very dangerous and potentially lethal side effect was regarded as an unacceptable side effect, especially since it was clear that the patients receiving 750 mg/kg of were suffering from varying levels of lactic acidosis.

Accordingly, all post-bypass injections were reduced by 50% for the remaining 9 FDP-treated patients, to 125 mg/kg at 2 hours and 6 hours post-bypass. This still involved a total injection load of 500 mg/kg for most patients, which translates to about 50 grams of FDP for most patients, injected over about 7 hours. These 9 patients were classified as the Stage 5b patients. They enjoyed substantial improvements in blood CK values, PAWP values, cardiac index, cardiac output, and LVSWI; however, this Stage 5b dosage also suffered from an unacceptably high occurrence rate for atrial fibrillation. 5 of the 9 patients tested at the Stage 5b dosages suffered atrial fibrillation.

This sample size is very small, and data are not statistically reliable from a sample this small; in addition, confirmatory tests have not yet been carried out to ensure that lactic acid accumulation is indeed the true causative agent in increasing the risk or occurrence rate of atrial fibrillation. Nevertheless, these data must be regarded with both (i) a realization of the importance of atrial fibrillation, when it occurs among patients who have been subjected to open-chest surgery requiring cardiopulmonary bypass, and (ii) an understanding of the biochemical pathways of glycolysis, which cause the large majority of exogenous FDP to be converted to lactic acid in ischemic tissue.

Accordingly, when all of these factors are taken into account, even though the sample sizes were very small in the Stage 5a and Stage 5b trials, the data from those tests indicate that if FDP injection dosages approximating these quantities are used in patients undergoing surgery involving CPB, the FDP injections probably should be accompanied by both (i) careful monitoring of the patient to ensure that lactic acid buildup remains within safe and expected ranges during after the CPB period; and (ii) at least one agent, such as sodium bicarbonate or dichloroacetate., which can suppress lactic acidosis, either by buffering blood acidity, or by diverting any accumulating pyruvate into the acetyl-CoA pathway, so that it cannot be subsequently converted into lactic acid.

TIMING OF FDP INJECTIONS

In the various tests described in the Examples (excluding the "Stage 2" tests, which involved adding FDP to the cardioplegia solution only), FDP was infused into the patients over periods lasting from about 20 to 30 minutes, commencing at times ranging from about 10 to about 30 minutes before circulatory bypass began.

In these patients, no major differences in the results were seen when varying commencement times were used. Accordingly, it is believed that the exact timing of commencement is not critical during the roughly 1-hour period before bypass begins, so long as a sufficient quantity of FDP is allowed to permeate into the heart and lungs before bypass begins. Accordingly, it is recommended that FDP injection should begin at least about 10 to 15 minutes, and up to about 30 minutes, before circulatory bypass begins. If commencement times more than 30 minutes before bypass begins are used, and/or if more than a few minutes elapse after FDP injection is terminated before bypass begins, such administration should be evaluated carefully, since the half-life of FDP in circulating blood is relatively short, on the order of only about 15 minutes.

In general, the preferred timing should commence roughly 20 minutes before bypass begins; when possible, the infusion should be continued until the time bypass is commenced and flow through the heart and lungs is disrupted.

It should also be noted that if dichloroacetate (abbreviated as DCA) is used as an adjunctive agent to help suppress and reduce the formation of lactic acid from the injected FDP, the DCA probably should be administered in advance of the FDP, because of its mechanism of action.

DCA increases the activity of an enzyme complex, called pyruvate dehydrogenase (PDH). As noted in the Background section, in glycolysis, FDP is broken apart to form two molecules of pyruvate. The resulting pyruvate will then go down either of two different pathways. If oxygen is present, pyruvate will be converted to a compound called acetyl-CoA, which is subsequently oxidized all the way to carbon dioxide and water; however, if inadequate supplies of oxygen are present, the pyruvate will be converted into lactic acid.

Unless cells are deeply and profoundly hypoxic, which does not occur in heart tissue during CPB surgery, when DCA increases the activity level of the PDH enzyme, the activated PDH enzyme will more rapidly convert pyruvate molecules into acetyl-coA. This reaction irreversibly commits the pyruvate to the Krebs cycle pathway, which leads to carbon dioxide and water before those molecules of pyruvate can be converted into lactic acid. In this manner, DCA can "push" pyruvate molecules away from the lactic acid pathway, and into a completely different metabolic pathway that leads to different products. However, in order for this to occur, the DCA preferably should be administered to the patient a sufficient period of time in advance, before FDP is injected into the patient, in order to allow the DCA to activate the PDH enzyme complex before any pyruvate is generate, so that any pyruvate will be promptly grabbed and converted into acetyl-CoA, by activated PDH complexes which should be already prepared and waiting for pyruvate formation.

One other factor involving the timing of FDP injections also should be taken into account. Because of various physiological and biochemical factors that go beyond the scope of this current invention, and which have not yet been specifically evaluated by any tests, the Inventors herein believe and anticipate that infusion of FDP over a 24 or 48 hour period, before surgery begins, may offer certain additional benefits, above and beyond the benefits that can be provided by administering FDP to a patient during the 1-hour period prior to bypass. Such additional benefits are believed likely to result from an ability of FDP to modify certain activities and behaviors of endothelial cells, which line the interiors of blood vessels, including capillaries. More extensive tests to evaluate these possible effects of FDP, when infused into circulating blood over longer periods of time (such as about 24 hours or longer), are currently being planned and organized.

Accordingly, in order to satisfy the best mode requirement for the current invention, the Inventors hereby state that they anticipate that the best mode of carrying out this invention is likely to involve both of the following treatments, co-administered together: (i) infusion of FDP into the patient for a period of about 24 hours or longer, most probably at relatively low dosages such as in the range of about 20 to about 100 mg/kg per hour, to take full advantage of FDP's ability to modify endothelial cell function and/or various other cellular or physiological activities; and in addition, (ii) infusion of a higher dosage of FDP into the patient (such as 250 mg/kg) during a relatively brief period such as about 20 minutes) before cardiopulmonary bypass begins, to "preload" the heart and lungs with FDP in quantities that will help the heart and lungs endure the ischemic bypass period with less stress, and lower levels of damage.

INFUSION OF FDP IN CARDIOPLEGIA

As indicated by the dosages used in Stages 2 and 3, FDP can be infused into heart muscle by adding it to cardioplegia fluid. Cardioplegia solution (the "plegia" suffix indicates "paralyzed") is infused into the heart via the coronary arteries (or coronary veins, if "retrograde" cardioplegia is used) for at least three purposes: (i) it contains potassium, which helps stop the heartbeat; (ii) it is chilled, to reduce the temperature of the heart muscle, to reduce oxygen demand and ischemic damage during the bypass period; and, (iii) it contains some quantity of oxygen, so that the heart is not completely deprived of all oxygen supply during bypass.

In general, the Stage 2 tests were a baseline study, to make sure no unexpected effects arose if FDP was added to a cardioplegia solution. Any potential benefits from the cardioplegia-only tests in Stage 2 were not expected to be substantial, so only 5 patients were tested in each of the three Stage 2 subcategories listed above. No adverse effects were seen, and no important differences between untreated (placebo) patients, and patients treated with FDP but only cardioplegia solution.

As noted above, Stage 3 treatments effectively combined the 250 mg/kg pre-bypass dosage of Stage 1 with the 5 mM cardioplegia dosage of Stage 2. These treatments were administered to 15 treated patients, compared against 15 control (placebo) patients. The results in various hemodynamic pumping parameters tended to be slightly better than the Stage 1 (pre-bypass only) results, which suggests that additional of FDP to cardioplegia is probably worthwhile.

In addition, there was a notable drop in occurrence rates for atrial fibrillation in the Stage 3 tests (with both pre-bypass and cardioplegia infusion), while there was no corresponding drop in occurrence of atrial fibrillation in the Stage 1 tests (pre-bypass only). Indeed, as shown in FIG. 11, it should be noted that in the Stage 1 tests, there was actually an increase in occurrence of atrial fibrillation in FDP-treated patients (4 out of 10 treated patients), compared to placebo-treated patients (2 out of 10 control patients). That increase is believed to be entirely due to a random event, occasioned by the small sample sizes.

Nevertheless, the fact that Stage 3 results showed a strong reduction in atrial fibrillation, while Stage 1 results did not, tends to suggest that adding FDP to cardioplegia solution is likely to be beneficial and worthwhile, in addition to pre-bypass infusion.

It is recognized that the data on this point are not yet conclusive; accordingly, the addition of FDP to cardioplegia solution should be regarded as a preferred, but not essential, embodiment of the invention herein.

DATA INDICATING THE BENEFITS OF FDP IN SURGERY USING CPB

The efficacy of FDP in protecting heart muscle against ischemic damage during CABG surgery (which is one of the most commonly-performed types of surgery that uses cardiopulmonary bypass) has been demonstrated in a number of ways. All of these ways are independent of each other, to some extent; however, they all correlate well with each other, which confirms that FDP treatment apparently provides substantial and potentially very important protective benefits for heart muscle, so long as lactic acid does not accumulate at levels that increase the risk of atrial fibrillation.

Figure 4:
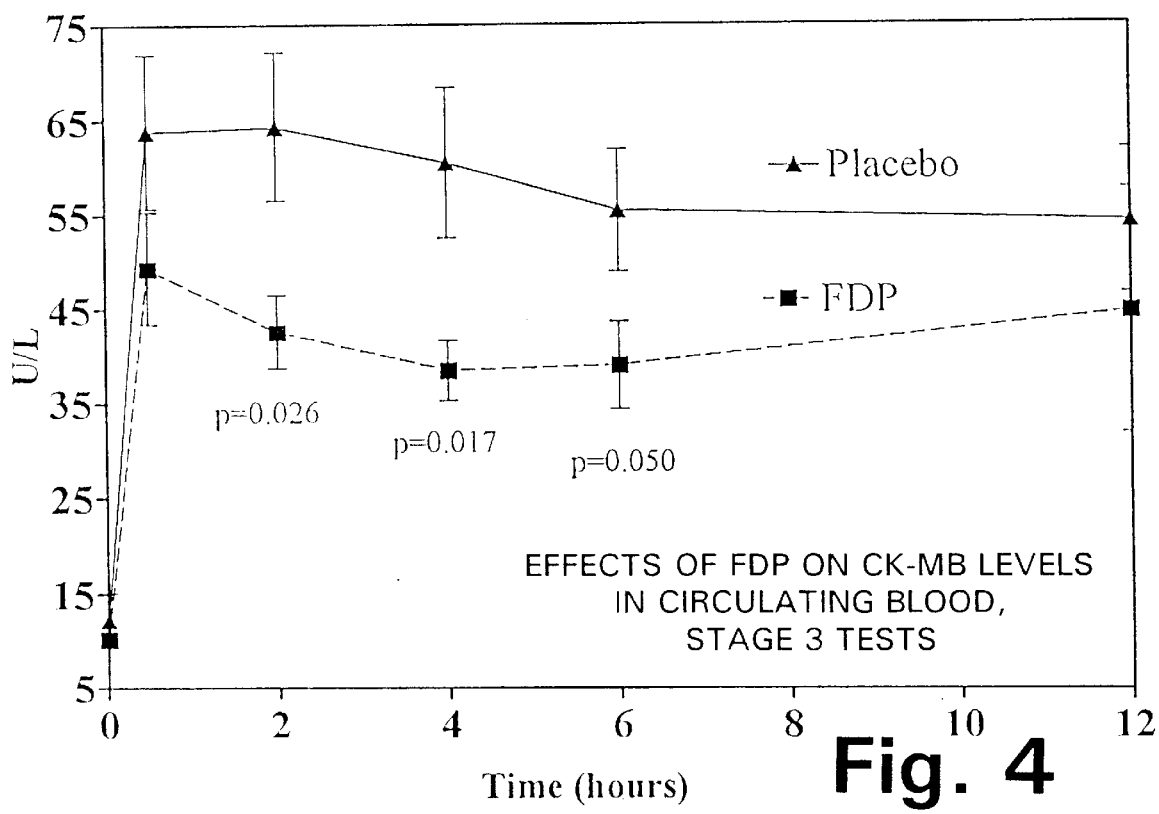
FIG. 4 is a graph indicating the results of blood plasma assays that measured a particular CK isozyme known as CK-MB, in the Stage 3 tests. As in the Stage 1 tests, pre-bypass injection of FDP substantially reduced levels of CK-MB in circulating blood plasma.

As mentioned in the Background section, levels of the creatine kinase (CK) enzyme in circulating blood provide a very useful indicator of the extent of heart cell death and permanent tissue damage, in cardiac patients. In the Stage 1 tests, total CK levels were measured; those values are shown in FIGS. 1 and 3. In the other stages which were carried out later, more specialized assays were used to measure only the CK-MB isozyme, which is predominant in heart cells; those results are shown in FIG. 4, for the Stage 3 tests. As described in the example and shown in the figures, FDP treatment substantially reduced CK levels in blood plasma, in both sets of tests. The result is important, since it clearly shows that FDP injection before circulatory bypass began significantly reduced the extent of heart cell death during the CABG surgery.

The hemodynamic (pumping performance) effects of FDP in CABG patients were measured by evaluating PAWP values, cardiac output, cardiac index, and "left ventricular stroke work index" (LVSWI), all of which are standard measurements in cardiac patients, as briefly summarized in the Background section. As disclosed in the examples and figures, injection of FDP prior to bypass caused substantial improvements in all of these hemodynamic values, showing that the FDP-treated hearts were substantially more capable of doing their necessary pumping work.

In addition to the CK and hemodynamic indices discussed above, three other important evaluative measurements were taken of patients in the Stage 1 and Stage 3 trials.

(1) One such indicator involves the amount of time (in hours) that treated vs. untreated patients had to be administered a vasodilating drug, glyceryl trinitrate (abbreviated as GTN). Since different dosages are required among different patients having different body weights, to achieve the necessary effects in each patient, the most relevant parameter for indicating vasodilator use is the number of hours each patient had to be maintained on GTN.

The decision as to how long vasodilators should be used, for any specific patient, is made by a treating physician rather than the patient, and every physician who cares for such patients is acutely aware that vasodilators can cause potentially dangerous side effects. Accordingly, physicians terminate vasodilator use, as soon as they think it is safe to do so, in any specific patient, and duration of use is a reliable indicator of how well and how quickly a patient is recovering from surgery.

As shown in FIG. 8, FDP treatment reduced (by roughly half) the amount of time that patients had to be treated with vasodilators, in both the Stage 1 and Stage 3 tests. This indicates highly useful and beneficial effects from the FDP treatment.

(2) A second indicator measured the amount of time (in hours) that treated vs. untreated patients had to be administered an inotropic drug, dopamine. Inotropic drugs will drive a heart to beat harder and with more pressure-generating force, causing it to pump out more blood with each heartbeat. This may sound very useful and productive, but it is a dangerous approach, used only when necessary and terminated as soon as possible, since inotropic drugs can provoke potentially dangerous or even deadly dysrhythmias in the heartbeat, and can cause other problems as well.

As shown in FIG. 9, pre-bypass injection of FDP reduced the amount of time patients had to be treated with this inotropic drug, by more than half, in both the Stage 1 and Stage 3 trials. This was another very useful and beneficial effect.

(2) A third measurement involved the amount of time (in hours) that treated vs. untreated patients had to be kept in an intensive care unit (ICU), before a patient was judged by his/her doctor to have stable enough to allow that patient to be moved safely into a normal hospital room.

As shown in FIG. 10, pre-bypass injection of FDP reduced the amount of time that patients had to be kept in the ICU by roughly half, in both the Stage 1 and Stage 3 trials. This was yet another very useful and beneficial effect.

All of these results (which are compiled in Table 3, showing mean values and standard deviations) are important and highly beneficial, and clearly support the conclusion that pre-bypass injection of FDP can reduce the amount of damage inflicted on hearts during CPB surgery.

TABLE 3

Reduction of Vasodilator, Inotrope, and ICU Requirements
By Pre-Bypass FDP Injection before CABG Surgery
(mean values ± std. deviation, in hours)

|  | Stage 1 | Stage 3 |
| --- | --- | --- |
| Vasodilator requirements (GTN, in hours) |  |  |
| Placebo: | 35.4 ± 11.8 | 30.5 ± 29.3 |
| FDP-treated: | 16.7 ± 2.1 | 19.0 ± 3.0 |
| Inotrope requirements (dopamine, in hours) |  |  |
| Placebo: | 7.9 ± 23.6 | 34.6 ± 32.2 |

TABLE 3-continued

Reduction of Vasodilator, Inotrope, and ICU Requirements
By Pre-Bypass FDP Injection before CABG Surgery
(mean values ± std. deviation, in hours)

|  | Stage 1 | Stage 3 |
| --- | --- | --- |
| FDP-treated: | 3.1 ± 2.1 | 15.8 ± 6.5 |
| Time in Intensive Care Unit (hours) |  |  |
| Placebo: | 20.3 | 36.9 |
| FDP-treated: | 10.1 | 20.3 |

In addition to all of the foregoing, two additional types of data also support the conclusion that FDP indeed help protect patients undergoing CABG or other CPB surgery. As noted in the Background section, those two types of data involve (i) the likelihood and occurrence rates for atrial fibrillation, and (ii) elevations in pulmonary vascular resistance (PVR), also called pulmonary hypertension. These two types of evidence are so important that each is discussed under its own heading.

REDUCTION OF PULMONARY VASCULAR RESISTANCE (PVR)

As mentioned briefly in the Background section, another hemodynamic indicator is also very important in any surgery involving cardiopulmonary bypass, even though it does not strictly involve the heart. This indicator is called "pulmonary vascular resistance" (PVR), and it measures the drop in blood pressure in a pulmonary vein, compared to a pulmonary artery. This drop in blood pressure is caused not by the heart, but by the amount of resistance in the capillaries inside the lungs. Elevated PVR levels (pulmonary hypertension) indicate that blood is not flowing properly through the lungs, due to problems such as edema, inflammation due to an allergic response, immune response, histamines or cytokines, or other forms of tissue stress or damage inside the lungs.

Since it measures a drop in pressure, PVR can be expressed in metric terms (dynes-second/$cm^3$), or in terms of millimeters of mercury column. It can also be expressed as a PVR index (PVRI), by dividing the metric form of PVR by the surface area (in square centimeters) of the body of a patient, to give values in dynes-second/$cm^5$.

In the United States, certain pulmonary pressure levels are usually monitored during any surgery involving cardiopulmonary bypass, so that surgeons and anesthesiologists will be alerted promptly if edema, tissue inflammation, or similar problems begin to threaten lung functioning and require prompt corrective action. PVR levels can be calculated from such measurements.

The results indicated that administration of FDP caused a substantial benefit in preventing large increases in PVR levels during the surgery. This was unexpected, since elevations in PVR are generated in the lungs, rather than in the heart, and the tests were designed to evaluate the effects of FDP on the heart. However, it should be noted that intravenous injection of FDP into a patient before bypass commences will cause the FDP to permeate not just into the heart muscle, but into lung tissue as well, and once cardiac bypass begins, the lungs are almost always bypassed as well, as indicated by the phrase "cardio-pulmonary bypass".

Based on the highly favorable PVR data, it is believed that some type of cellular reaction involving FDP apparently occurred inside the lungs, which helped the lungs resist edema, tissue inflammation, and possibly other forms of stress or damage during the ischemic bypass period.

Based on the PVR data, FDP treatment also may have helped the lung tissue suppress, or possibly resist and withstand, the release of histamine and/or one or more cytokines inside the lung tissue, since histamine and various cytokines are known to be very important factors which aggravate tissue swelling and fluid accumulation inside the lungs. Histamine and cytokine levels in fluids and tissues can be measured by various means, in both lung fluids and lung tissue, and the possible correlations between FDP treatment, lower PVR values, and histamine and cytokine levels, can be further evaluated, if desired.

FORMULATIONS, DOSAGES, AND MODES OF ADMINISTRATION

Any suitable (i.e., pharmacologically acceptable) salt of FDP can be used, such as a sodium salt, or divalent salts such as calcium or magnesium salts, or mixtures thereof. In general, potassium salts should not be administered intravenously, since an abrupt injection might interfere with cardiac functioning and certain other cellular functions.

Isomers other than fructose-1,6-diphosphate cannot be used. Although certain other isomers (including fructose-2, 6-diphosphate) occur naturally in cells, they serve other purposes and are not created or consumed as intermediates in the glycolysis pathway.

As mentioned above, U.S. Pat. No. 5,731,291 (Sullivan and Marangos, 1998) discloses a method of "partially lyophilizing" FDP to a point where about 10 to about 20% (by weight) residual water remains in the cake or powder. Such preparations can be created in completely sterile form inside sealed watertight vials, ready for reconstitution into an injectable liquid by mixing the lyophilized FDP with sterile water or saline solution.

The FDP formulation can be infused intravenously either as a solution of up to about 10% FDP by weight, or after dilution into sterile infusion bags containing 5% dextrose solution, 0.9% saline, Ringer's lactate, or other conventional intravenous fluids (excluding formulations used for parenteral feeding or blood transfusions).

Since FDP is a short-lived intermediate which is quickly consumed by glycolysis, it is believed that FDP preferably should be infused over a sustained period (such as at least about 10 minutes, up to about 30 to 60 minutes), rather than in a single bolus injection. Because of various pharmacokinetic factors, a single injection is likely to be consumed and converted into other metabolites rather quickly; by contrast, a sustained infusion will help "load up" cells with more FDP than they need at any particular moment, and will increase the levels of FDP that are present in cells when they begin suffering from ischemia, after circulatory bypass begins. Infusion preferably should begin at least about 10 minutes, up to about 30 to 60 minutes, before the onset of circulatory bypass. If desired, additional FDP can be continually added to the circulating blood while the patient is on bypass; although this FDP will not pass through the heart during bypass, it may be able to help minimize stress and damage in other organs or tissues; in addition, the presence of FDP in the blood, when bypass ends and the heartbeat is started up again, may help the patient's heart recover its proper functioning more rapidly or stably.

It should also be noted that FDP can be dissolved in sterile water or saline solution, and that solution can be inhaled directly into the lungs, via a nebulizer. If desired, this mode of administration can also be evaluated for the purpose of reducing pulmonary vascular resistance.

EXAMPLES

Example 1

Surgical and Test Procedures in Stage 1 Tests

All testing procedures described herein were carried out at the Harefield Hospital, in Harefield, England, under the supervision of a qualified cardiac anesthesiologist. These tests were initiated and sponsored by Cypros Pharmaceutical Corporation (the assignee and applicant herein), which obtained approval from the United States Food and Drug Administration prior to carrying out these Phase II human clinical trials, so that the data gathered in these tests could subsequently be used in a United States drug approval application. Phase I trial requirements (to establish baseline values for FDP using tests on healthy volunteers) were waived by the U.S.F.D.A., since FDP is a naturally occurring biochemical that occurs only as a short-lived intermediate which is quickly consumed during glycolysis.

Twenty patients were selected for coronary artery bypass graft surgery, usually based on complaints of chest pain or evidence of myocardial infarction. These patients underwent routine screening and evaluation to determine that their coronary artery occlusions were severe enough to warrant artery grafting rather than balloon angioplasty or other less-invasive procedures.

Anesthesia was induced by standard techniques, using inhalation agents, injectable agents, or both, as determined for each patient by a skilled anesthesiologist. There were no significant differences in anesthesia methods between the FDP treatment group and the untreated control group.

Throughout surgery, anesthesia was maintained with a combination of agents that sustained unconsciousness, paralysis, and immobility; this required the use of a mechanical ventilator before cardiac bypass began and after it ended. Patients were monitored with various instruments either situated externally (e.g., to analyze exhaled gases), upon the surface of their body (e.g., a stethoscope and EKG recording electrodes), or within their body, through a normal orifice (such as a temperature probe placed in the esophagus) or by insertion through the skin (e.g., pressure recording catheters were passed through an incision in the groin or neck, and advanced into the chambers of the heart or a pulmonary artery).

The chest was opened by longitudinal incision over and through the sternal bone. The chest wall was spread open and held apart with a chest retractor (also called an "alligator" in England).

An arterial graft was taken from either a mammary artery, inside the chest, or a saphenous vein, in a leg; there was no statistical difference between groups. Any branches of the vein graft were carefully sutured shut, to make sure it was watertight except for the normal orifices at each end.

An injection of 250 mg/kg of a stable formulation of a suitable sodium salt of FDP was used. This salt mixture contained a ¾ saturation level of sodium (i.e., there were enough sodium ions present in the solution to bond ionically to ¾ of the four acidic groups on each molecule of FDP, while the pH was sufficiently low that the remaining ¼ of the organic acid groups remained non-ionized). This FDP salt was injected into a central vein (such as an internal jugular vein) or a peripheral vein (such as an arm vein), beginning up to about 30 minutes before the start of circulatory bypass using a heart-lung machine. This infusion was diluted into a larger volume (usually about 250 to 450 milliliters) of a compatible, sterile intravenous infusion fluid, such as a solution of 5% dextrose in water.

A matched placebo was injected into patients in the control population. The anesthesiologist(s) working on any specific patient were unaware whether they had infused that patient with FDP or a placebo.

The bypass machine was prepared by filling the pumping chamber with either blood or an oxygenated solution compatible with blood; this process is known as pump priming. The aorta was clamped, punctured, and received the effluent hose from the bypass machine. The right atrium, or one of the large venous vessels leading to it, was punctured and received the hose which carried deoxygenated blood to the bypass machine. Additional cannulas were inserted into the coronary arteries and the coronary (venous) sinus, to allow independent perfusion of the heart muscle with cold "cardioplegia" solution containing high concentrations of potassium, to cause the heart to stop beating during surgery. Once bypass was established, the patient's entire body and brain (excluding his/her heart) received all needed oxygen and nutrients by additions to the blood circulating outside his or her body, through the bypass machine. The patient's heart, however, was being perfused only by the cardioplegia solution, and was suffering the ischemic insult that necessarily accompanies this type of surgery.

The saphenous vein segment or mammary artery end was sutured into place on the surface of the heart, to create a new coronary artery passageway which circumvented and bypassed an obstructed native coronary artery. After suturing and pressure testing were completed, the heartbeat was restarted, usually with the aid of electric shock, which was often needed more than once due to the tendency of hearts to fibrillate as they are rewarmed and restarted after surgery. The hoses from the bypass machine were slowly clamped off, to test whether the patient's heart could regain adequate blood pumping pressure, and to allow continuing inspection for leakage from the sutured artery grafts. If all was well, the bypass hoses were removed from the aorta and right side of the heart, and their entry punctures were sutured shut. The basin formed by the pericardial membrane was again inspected for leakage, and plastic drainage tubes were inserted into the pericardial space and secured in position with sutures; these tubes passed through the skin at a location other than the site of the incision. The alligator jaws were closed and removed, and the divided sternal bone was wired shut using steel wire loops. The skin and soft tissues were closed, and the patient was returned to an intensive care unit with mechanical ventilator still operating, and various drains and intravenous cannulae in place.

After a period of recovery (usually several hours, depending on the condition of the patient), the mechanical ventilator was removed and the patient breathed on his/her own. Other interventions and monitors were withdrawn gradually, usually over a period of several days, as the patient regained strength and returned to an independent state.

Post-operative monitoring included EKG recording, CK enzyme concentrations in circulating blood, and measurements of heart function through invasive pressure monitoring catheters and echocardiography.

When FDP-pretreated patient populations were compared to untreated control populations, these measurements clearly demonstrated that injection of FDP, before cardiopulmonary bypass began, resulted in both (1) substantial reductions of heart cell damage (as measured by CK release into blood by ruptured cells), and (2) substantial reductions in the hemodynamic abnormalities and other manifestations of stress that are shown by hearts that have undergone bypass operations.

These results are shown graphically in the drawings. In these drawings, references to "AUC" refer to "area under the curve". These data points, calculated individually for each patient based on the data points measured for that patient over a span of several days, provide an overall numerical indication of how much total stress and damage a patient suffered, as measured by CK blood levels and elevated PAWP values which lasted for several days.

Various additional data from the Stage 1 tests are shown in FIGS. 8–11. As shown therein, the FDP dosage used in the Stage 1 tests reduced vasodilator and inotropic drug requirements after surgery, and also reduced the amount of time the patients had to stay in intensive care units after surgery.

The atrial fibrillation data for Stage 1 in FIG. 11 indicate that atrial fibrillation occurrence rates went up. However, this is believed to be a solely statistical error, based on the very small sample size used in Stage 1.

Example 2

Stage 2 Tests

As discussed above, various different FDP dosage regimens were tested, in a series of tests that were labelled as Stage 1 through Stage 5. The dosage regimen for each stage is discussed above, and is summarized in Table 1, also above.

Stage 2, which involved FDP added solely to cardioplegia solution, with no pre-bypass or post-bypass injections, was essentially a baseline test, to make sure nothing unexpected would happen when FDP was added to cardioplegia, before the Stage 3 tests began, using both pre-bypass and cardioplegia administration of FDP.

As expected, the results of the Stage 2 (cardioplegia-only) treatment were not significantly different from placebo treatment. However, this did not indicate a failure of the Stage 2 tests in any way; instead, when no adverse or unexpected effects were seen, this cleared the way for the expanded Stage 3 tests.

Example 3

Stage 3 Tests

As noted above, the Stage 3 tests involved a combination of the Stage 1 pre-bypass dosage, and the Stage 2 cardioplegia dosage.

The graphs in FIGS. 4 through 7 show the data gathered during the Stage 3 tests, in terms of the following parameters:

FIG. 4: CK-MB levels in circulating blood;

FIG. 5: "left ventricular stroke work index" (LVSWI) values;

FIG. 6: "cardiac index" (CI) values;

FIG. 7: "pulmonary vascular resistance" (PVR) values.

FIGS. 8 through 10 also provide bar graphs showing results from both the Stage 1 and Stage 3 trials, in terms of the following parameters:

FIG. 8: reductions in the amount of time FDP-treated patients had to remain in an intensive care unit (ICU) after CABG surgery, before the patients could be transferred to ordinary hospital rooms.

FIG. 9: reductions in the amount of dopamine (a potentially dangerous inotropic drug) that had to be used to stimulate the hearts of CABG patients after surgery; and, FIG. 10: reductions in the amount of glyceryl trinitrate (GTN, a vasodilator drug) that had to be used to stabilize CABG patients after surgery.

In addition, FIG. 11 shows the results of the atrial fibrillation occurrence rates for Stage 3, and for the other stages as well. It should be noted that atrial fibrillation occurrence rates were substantially decreased (i.e., improved) by the Stage 3 dosage regimen.

Example 4

Stage 4 Tests

The Stage 4 tests were a dose-response test, in which the pre-bypass dosage used in the Stage 1 tests was cut in half, from 250 mg/kg (which worked well in the Stage 1 tests, despite the upsurge in atrial fibrillation occurrence rate, which is believed to be solely a statistical artifact), to only 125 mg/kg in the Stage 4 tests. No FDP was added to the cardioplegia, and no post-bypass injections were used.

As expected, the results (in terms of slightly lower CK blood levels, slightly improved hemodynamic pumping performance, and lower levels of PVR) trended in positive and beneficial directions, but did not reach statistically significant levels. This confirmed that a pre-bypass dosage which is higher than 125 mg/kg is more effective and beneficial than a 125 mg/kg pre-bypass dosage.

Example 5

Stage 5 Tests

As described above, Stage 5 initially started out using 250 mg/kg pre-bypass, plus 250 mg/kg at 2 hours post-bypass, plus another 250 mg/kg at 6 hours post-bypass. This infusion of 750 mg/kg (almost 70 grams of FDP, for a patient weighing about 90 kg, which is about 200 pounds), over about a 7 hour period, caused significant levels of lactic acidosis. Although this very high dosage caused improvements in blood CK values, PAWP values, cardiac index, cardiac output, and LVSWI, it also became clear, fairly quickly, that this dosage was causing a very important drawback: 3 of the 6 patients tested at this dosage of FDP suffered atrial fibrillation.

Despite the very small sample size and the unreliability of statistical analyses when studying such small populations, the 50% occurrence rate for a very dangerous and potentially lethal side effect was regarded as an unacceptable side effect, especially since it was clear that the patients receiving 750 mg/kg of were suffering from varying levels of lactic acidosis.

Accordingly, all post-bypass injections were reduced by 50% for the remaining 9 FDP-treated patients, to 125 mg/kg at 2 hours and 6 hours post-bypass. This still involved a total injection load of 500 mg/kg for most patients, which translates to about 50 grams of FDP for most patients, injected over about 7 hours.

To facilitate analysis, Stage 5 was grouped into 2 subcategories: the initial 6 treatment patients (750 mg/kg total FDP) were referred to as Stage 5a patients, while the remaining 9 treatment patients (500 mg/kg total FDP) were referred to as Stage 5b patients.

The Stage 5b patients showed significant improvements in blood CK values, PAWP values, cardiac index, cardiac output, and LVSWI; however, the Stage 5b dosage still suffered from elevated occurrence rates for atrial fibrillation. 5 of the 9 patients tested at the Stage 5b dosages suffered atrial fibrillation. These data are indicated in FIG. 11.

This sample size is very small, and data are not statistically reliable from a sample this small; in addition, confirmatory tests have not yet been carried out to ensure that lactic acid accumulation is indeed the true causative agent in increasing the risk or occurrence rate of atrial fibrillation. Nevertheless, these data must be regarded with both (i) a realization of the importance of atrial fibrillation, when it occurs among patients who have been subjected to open-chest surgery requiring cardiopulmonary bypass, and (ii) an understanding of the biochemical pathways of glycolysis, which cause the large majority of exogenous FDP to be converted to lactic acid in ischemic tissue.

Accordingly, when all of these factors are taken into account, even though the sample sizes were very small in the Stage 5a and Stage 5b trials, the data from those tests indicate that if FDP injection dosages approximating these quantities are used in patients undergoing surgery involving CPB, the FDP injections probably should be accompanied by both (i) careful monitoring of the patient to ensure that lactic acid buildup remains within safe and expected ranges during after the CPB period; and (ii) at least one agent, such as sodium bicarbonate or dichloroacetate, which can suppress lactic acidosis, either by buffering blood acidity, or by diverting any accumulating pyruvate into the acetyl-CoA pathway, so that it cannot be subsequently converted into lactic acid.

Thus, there has been shown and described a new and useful method for reducing pulmonary hypertension, and for reducing the risk of atrial fibrillation, in patients who are being prepared for surgery requiring cardiopulmonary bypass. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Angelos, M. G., et al, "Fructose-1,6-diphosphate fails to limit early myocardial infarction size in a canine model," *Ann. Emerg. Med.* 22: 171–177 (1993)

Bickler, P. E., et al, "Fructose-1,6-bisphosphate stabilizes brain intracellular calcium during hypoxia in rats," *Stroke* 23: 1617–22 (1992)

Brunswick, R., et al, "Preservation of myocardium by infusion of fructose diphosphate following coronary occlusion," *Am J Cardiol* 49: 1008 (1982)

Cacioli, D., et al, "Haemorheological effects of fructose-1,6-diphosphate in patients with lower extremity ischaemia," *Curr Med Res Opin* 10: 668–74 (1988)

Cargnoni, A., et al, "Role of timing of administration in the cardioprotective effect of fructose-1,6-bisphosphate," *Cardiovasc Drugs Ther* 6: 209–17 (1992)

Crescimanno, M., et al, "Influence of fructose 1,6-diphosphate on the lung antioxidant defenses of mice with endotoxemia," *Pharmacol Res* 22: 74–75 (1990)

de la Torre, J. C. "Treatment of head injury in mice, using a fructose 1,6-diphosphate and dimethyl sulfoxide combination," *Neurosurgery* 37: 273–9 (1995)

Eddy, L. J., et al, "Lack of a direct metabolic effect of fructose, 1,6-diphosphate in ischemic myocardium," *Am J Physiol* 241: H576–83 (1995)

Farias, L. A., et al, "Prevention of ischemic-hypoxic brain injury and death in rabbits with fructose-1,6-diphosphate," *Stroke* 21: 606–13 (1990)

Farias, L. A., et al, "Effects of fructose-1,6-diphosphate, glucose and saline on cardiac resuscitation," *Anesthesiology* 65: 595–601 (1986)

Farias, L. A., et al, "Improved brain metabolism with fructose 1–6 diphosphate during insulin-induced hypoglycemic coma," Central University of Venezuela. *Am J Med Sci* 297: 294–9 (1989)

Galzigna, L., et al, "Some effects of FDP on rat myocardial tissue relate to a membrane stabilizing action," *Cell Biochem. Function* 7: 91–96 (1989)

Gobbel, G. T., et al, "Response of cerebral endothelial cells to hypoxia: modification by fructose-1,6-bisphosphate but not glutamate receptor antagonists," *Brain Res* 653: 23–30 (1994)

Grandi, A. M., et al, "Improved left ventricular function after short-term treatment with fructose-1,6-diphosphate: echocardiographic study in chronic ischemic heart disease and idiopathic dilated cardiomyopathy," *Clin Ther* 10: 372–80 (1988)

Granot, H., et al, "Successful treatment of irreversible hemorrhagic shock in dogs with fructose-1,6 diphosphate and dichloroacetate," *Circ Shock* 163–73 (1985)

Gregory, G. A., et al, "Fructose-1,6-bisphosphate reduces ATP loss from hypoxic astrocytes," *Brain Res* 516: 310–2 (1990)

Hardin, C. D., et al, "Metabolism of exogenously applied fructose 1,6-bisphosphate in hypoxic vascular smooth muscles" *Am J Physiol* 267: H2325–32 (1994)

Hassinen, I. E., et al, "Mechanism of the effect of exogenous fructose 1,6-bisphosphate on myocardial energy metabolism," *Circulation* 83: 584–93 (1991)

Janz, T. G., et al, "The effects of fructose-1,6-diphosphate on myocardial damage in acute coronary artery occlusion," *Resuscitation* 22: 45–54 (1991)

Kelleher, J. A., et al, "Energy metabolism in hypoxic astrocytes: protective mechanism of fructose-1,6-bisphosphate," *Neurochem Res* 20: 785–92 (1995)

Kuluz, J. W., et al, "Fructose-1,6-bisphosphate reduces infarct volume after reversible middle cerebral artery occlusion in rats," *Stroke* 24: 1576–83 (1993)

Lazzarino, G., et al, "Ischemia and reperfusion: effect of fructose-1,6-bisphosphate," *Free Radic Res Commun* 16: 325–39 (1992)

Lazzarino G., et al, "Protective effects of exogenously administered fructose-1,6-diphosphate from ischemia reperfusion damage induced on isolated rat heart," *Ital J Biochem* 38: 251A–253A (1989)

Marchionni, N., et al, "Hemodynamic and electrocardiographic effects of fructose-1,6-diphosphate in acute myocardial infarction," *Am J Cardiol* 56: 266–269 (1985)

Marchionni, N., et al, "Improved exercise tolerance by i.v. fructose-1,6-diphosphate in chronic, stable angina pectoris," *J Clin Pharmacol* 28: 807–11 (1988)

Markov, A. K., et al, "Hemodynamic, electrocardiographic, and metabolic effects of fructose diphosphate on acute myocardial ischemia," *Am Heart J* 100: 639–46 (1980)

Markov, A. K., "Hemodynamics and metabolic effects of fructose 1–6 diphosphate in ischemia and shock—experimental and clinical observations," *Ann Emerg Med* 15: 1470–7 (1986)

Markov, A. K., et al, "Increasing survival of dogs subjected to hemorrhagic shock by administration of fructose 1–6 diphosphate," *Surgery* 102: 515–27 (1987)

Munger, M. A., et al, "Effect of intravenous fructose-1,6-diphosphate on myocardial contractility in patients with left ventricular dysfunction," *Pharmacotherapy* 14: 522–8 (1994)

Myers, J., et al, "Effect of fructose-1,6-diphosphate on exercise capacity in patients with peripheral vascular disease," *Int J Sports Med* 11: 259–262 (1990)

Nakai, T., et al, "Beneficial effects of fructose-1,6-diphosphate infusion on liver regeneration after ischemic liver injury," *Gastroenterology Japan* 26: 611–8 (1991)

Pasque, M. K., et a, "Metabolic intervention to affect myocardial recovery following ischemia," *Annals of Surgery* 200: 1–12 (1984)

Sano, W., et al, "Beneficial effect of fructose-1,6-bisphosphate on mitochondrial function during ischemia-reperfusion of rat liver," *Gastroenterology* 108: 1785–92 (1995)

Tortosa, A., et al, "Fructose-1,6-bisphosphate fails to ameliorate delayed neuronal death in the CAl area after transient forebrain ischaemia in gerbils," *Neuropharmacology* 32: 1367–71 (1992)

Trimarchi, G. R., et al, "Neuroprotective activity of fructose-1,6-bisphosphate following transient forebrain ischemia in the Mongolian gerbil," *Japan J Pharmacol* 62: 215–22 (1993)

Trimarchi, G. R., et al, "Effects of fructose-1,6-bisphosphate on brain polyamine biosynthesis in a model of transient cerebral ischemia," *Life Sci* 54: 1195–204 (1994)

Zhang, J. N., et al, "Protective effect of exogenous fructose-1,6-diphosphate in cardiogenic shock," *Cardiovasc Res* 22: 927–32 (1988)

We claim:

1. A method of reducing a risk of atrial fibrillation in a human patient who undergoes surgery that involves cardiopulmonary bypass, comprising intravenously injecting into the patient, prior to commencing cardiopulmonary bypass, a liquid formulation containing fructose-1,6-diphosphate or a pharmacologically acceptable salt thereof, in a therapeutically effective quantity and manner which:

(i) causes the fructose-1,6-diphosphate to enter heart and lung tissue while the heart is still beating, before cardiopulmonary bypass begins; and, (ii) reduces occurrence rates for atrial fibrillation during recuperation from cardiopulmonary bypass surgery.

2. The method of claim 1, wherein the surgery that involves cardiopulmonary bypass is selected from the group consisting of:

(a) surgery to repair occluded coronary arteries;

(b) surgery to repair heart valves;

(c) surgery to correct cardiac arrhythmias;

(d) surgery to remove heart muscle tissue to increase contact between a ventricular wall and oxygenated blood;

(5) heart transplant surgery;

(6) lung transplant surgery; and (7) surgery to correct a congenital heart disease.

3. The method of claim 1, wherein the fructose-1,6-diphosphate or salt thereof is intravenously infused into the patient over a period of at least 15 minutes.

4. The method of claim 1, wherein fructose-1,6-diphosphate is intravenously injected into the patient at a dosage of at least 100 milligrams of fructose-1,6-diphosphate per kilogram of patient body weight.

5. The method of claim 1, wherein fructose-1,6-diphosphate is co-administered to a patient along with a second agent that suppresses lactic acidosis in circulating blood.

6. The method of claim 5, wherein the second agent that suppresses lactic acidosis in circulating blood is selected from the group consisting of:
   a. alkalizing agents that are pharmacologically acceptable for intravenous injection into circulating blood; and,
   b. dichloroacetate.

7. A method for both (a) reducing pulmonary vascular resistance and (b) reducing a risk of atrial fibrillation, following surgery that involves cardiopulmonary bypass, comprising intravenously injecting into a human patient, prior to commencing cardiopulmonary bypass, a liquid formulation containing fructose-1,6-diphosphate or a pharmacologically acceptable salt thereof, in a therapeutically effective quantity and manner which:
   (i) causes the fructose-1,6-diphosphate to enter heart and lung tissue while the heart is still beating, before cardiopulmonary bypass begins;
   (ii) reduces occurrence rates for atrial fibrillation during recuperation from the surgery; and,
   (iii) reduces pulmonary vascular resistance during recuperation from the surgery.

8. The method of claim 7, wherein the surgery that involves cardiopulmonary bypass is selected from the group consisting of:
   (a) surgery to repair occluded coronary arteries;
   (b) surgery to repair heart valves;
   (c) surgery to correct cardiac arrhythmias;
   (d) surgery to remove heart muscle tissue to increase contact between a ventricular wall and oxygenated blood;
   (5) heart transplant surgery;
   (6) lung transplant surgery; and
   (7) surgery to correct a congenital heart disease.

9. The method of claim 7, wherein the fructose-1,6-diphosphate or salt thereof is intravenously infused into the patient over a period of at least 15 minutes.

10. The method of claim 7, wherein fructose-1,6-diphosphate is intravenously injected into the patient at a dosage of at least 100 milligrams of fructose-1,6-diphosphate per kilogram of patient body weight.

11. The method of claim 7, wherein fructose-1,6-diphosphate is co-administered to a patient along with a second agent that suppresses lactic acidosis in circulating blood.

12. The method of claim 11, wherein the second agent that suppresses lactic acidosis in circulating blood is selected from the group consisting of:
   a. alkalizing agents that are pharmacologically acceptable for intravenous injection into circulating blood; and,
   b. dichloroacetate.

* * * * *